(12) United States Patent
Gilbert et al.

(10) Patent No.: US 6,530,887 B1
(45) Date of Patent: Mar. 11, 2003

(54) ULTRASOUND PROBE WITH INTEGRATED ELECTRONICS

(75) Inventors: Jeffrey M. Gilbert, El Cerrito, CA (US); Alice M. Chiang, Weston, MA (US); Steven R. Broadstone, Woburn, MA (US); Gary Madison, Lexington, MA (US); Albert Horst, Westford, MA (US); Liang-Min Wang, Northboro, MA (US)

(73) Assignee: TeraTech Corporation, Burlington, MA (US)

( * ) Notice: Subject to any disclaimer, the term of this patent is extended or adjusted under 35 U.S.C. 154(b) by 0 days.

(21) Appl. No.: 09/449,780

(22) Filed: Nov. 26, 1999

Related U.S. Application Data

(63) Continuation-in-part of application No. PCT/US98/02291, filed on Feb. 3, 1998, which is a continuation-in-part of application No. 08/965,663, filed on Nov. 6, 1997, which is a continuation of application No. PCT/US97/24291, filed on Dec. 23, 1997, which is a continuation-in-part of application No. 08/773,647, filed on Dec. 24, 1996, now Pat. No. 5,904,652.

(60) Provisional application No. 60/140,430, filed on Jun. 22, 1999, and provisional application No. 60/036,837, filed on Feb. 3, 1997.

(51) Int. Cl.[7] ................................................ A61B 8/00
(52) U.S. Cl. ...................................................... 600/459
(58) Field of Search ................................. 600/437, 443, 600/444, 447, 459

(56) References Cited

U.S. PATENT DOCUMENTS

| 4,573,477 A | 3/1986 | Namekawa et al. ........ 128/663 |
|---|---|---|
| 4,622,977 A | 11/1986 | Namekawa et al. ........ 128/663 |
| 4,759,375 A | 7/1988 | Namekawa ................ 128/663 |
| 5,295,485 A | * 3/1994 | Shinomura et al. ......... 600/443 |
| 5,590,658 A | 1/1997 | Chiang et al. ......... 128/661.01 |
| 5,609,155 A | 3/1997 | Guracar ................ 128/661.09 |
| 5,615,679 A | 4/1997 | Ri et al. ................ 128/660.05 |
| 5,690,114 A | 11/1997 | Chiang et al. ......... 128/661.01 |
| 5,715,823 A | * 2/1998 | Wood et al. ................ 600/437 |
| 5,722,412 A | * 3/1998 | Pflugrath et al. ........... 600/443 |
| 5,758,649 A | 6/1998 | Iwashita et al. ....... 128/662.03 |
| 5,763,785 A | * 6/1998 | Chiang ........................ 73/609 |
| 5,795,297 A | 8/1998 | Daigle ........................ 600/447 |
| 5,817,024 A | 10/1998 | Ogle et al. .................. 600/447 |
| 5,839,442 A | 11/1998 | Chiang et al. ......... 128/661.01 |
| 5,860,930 A | 1/1999 | Guracar ...................... 600/455 |
| 5,893,363 A | 4/1999 | Little et al. ................ 600/447 |
| 5,904,652 A | 5/1999 | Gilbert et al. .............. 600/447 |
| 5,957,846 A | 9/1999 | Chiang et al. .............. 600/447 |
| 5,964,709 A | 10/1999 | Chiang et al. .............. 600/447 |
| 6,060,030 A | 5/2000 | Vara et al. .................. 600/437 |
| 6,106,472 A | 8/2000 | Chiang et al. .............. 600/447 |
| 6,111,816 A | 8/2000 | Chiang et al. ................. 367/7 |
| 6,142,946 A | 11/2000 | Hwang et al. .............. 600/459 |

OTHER PUBLICATIONS

Strassberg, Dan, "Despite Threats from USB and Firewire, IEEE 488 ain't down yet," *EDN Electrical Design News* 43(15) :67–80 (1998).

* cited by examiner

Primary Examiner—Francis J. Jaworski
Assistant Examiner—Maulin Patel
(74) Attorney, Agent, or Firm—Bowditch & Dewey, LLP

(57) ABSTRACT

A hand-held ultrasound probe system includes integrated electronics within an ergonomic housing. The electronics includes control circuitry, beamforming and circuitry transducer drive circuitry. The probe electronics communicates with a host computer using an industry standard high speed serial bus.

40 Claims, 18 Drawing Sheets

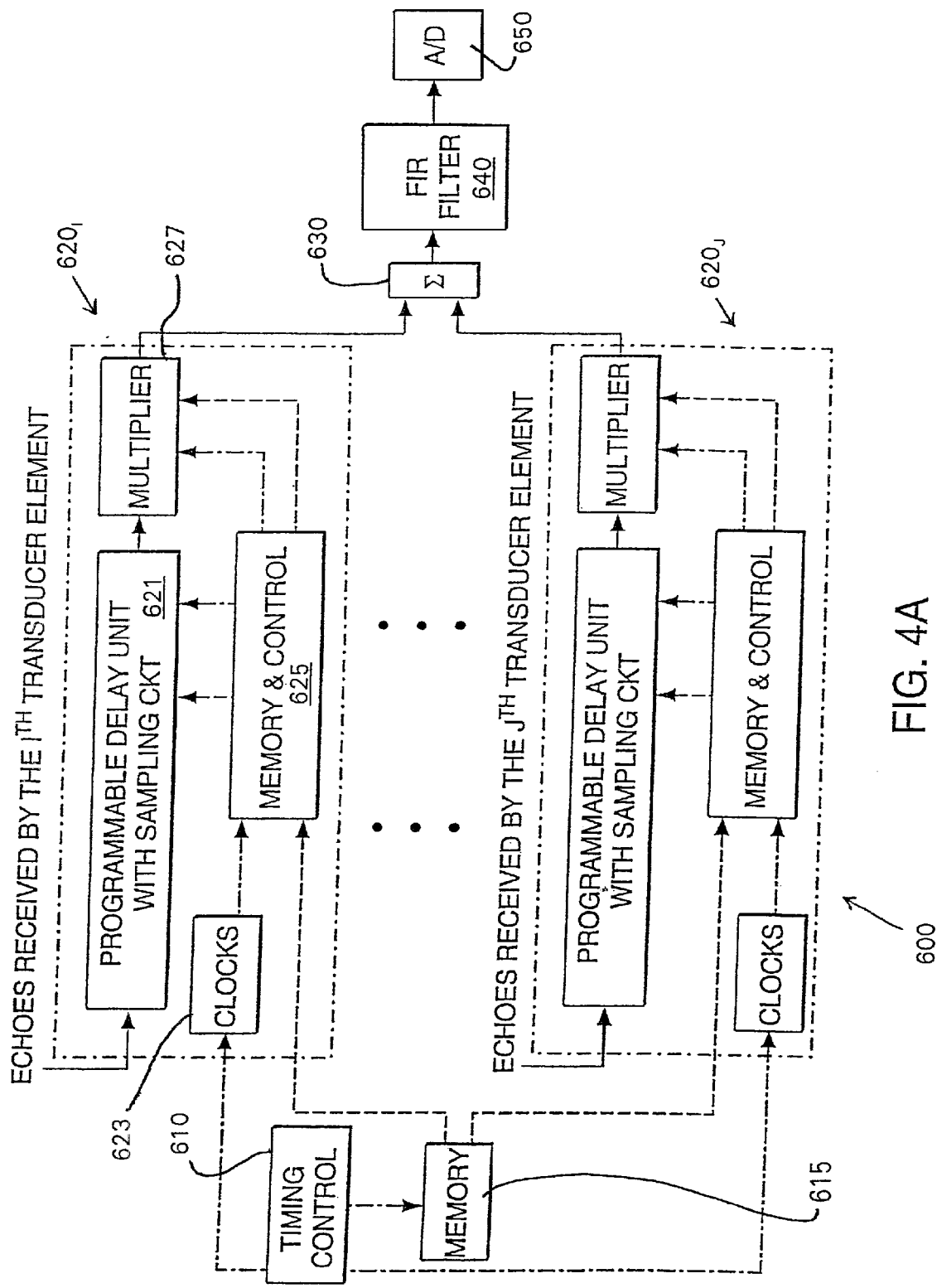

ULTRASOUND PROBE WITH INTEGRATED ELECTRONICS

RELATED APPLICATIONS

This application claims the benefit of U.S. Provisional Application No. 60/140,430, filed on Jun. 22, 1999 which is a continuation-in-part to International Application No. PCT/US98/02291, filed on Feb. 3, 1998 which is a continuation-in-part application of U.S. Ser. No. 08/965,663, filed on Nov. 6, 1997,which is a continuation-in-part application of U.S. Ser. No. 60/036,837 filed on Feb. 3, 1997. This application is also a continuation to International Application No. PCT/US97/24291 filed on Dec. 23, 1997, now U.S. Ser. No. 09/203,877 filed on Dec. 2, 1998, which is a continuation-in-part application of U.S. Ser. No. 08/773,647 filed on Dec. 24, 1996, now U.S. Pat. No. 5,904,652. The above applications are all incorporated herein by reference in their entirety.

BACKGROUND

Conventional ultrasound imaging systems typically include a hand-held probe coupled by cables to a large rack-mounted console processing and display unit. The probe typically includes an array of ultrasonic transducers which transmit ultrasonic energy into a region being examined and receive reflected ultrasonic energy returning from the region. The transducers convert the received ultrasonic energy into low-level electrical signals which are transferred over the cable to the processing unit. The processing unit applies appropriate beam forming techniques to combine the signals from the transducers to generate an image of the region of interest.

Typical conventional ultrasound systems include a transducer array each transducer being associated with its own processing circuitry located in the console processing unit. The processing circuitry typically includes driver circuits which, in the transmit mode, send precisely timed drive pulses to the transducer to initiate transmission of the ultrasonic signal. These transmit timing pulses are forwarded from the console processing unit along the cable to the scan head. In the receive mode, beamforming circuits of the processing circuitry introduce the appropriate delay into each low-level electrical signal from the transducers to dynamically focus the signals such that an accurate image can subsequently be generated.

Because all of the circuitry is located remote from the probe, rather bulky cables tether the probe to the console processing unit. Typically, separate cables provide power and control signals to the probe head. Those cables administer a significant torque onto the probe head. To drive 128 transducers, at least 128 transmit/receive lines (one for each transducer) are typically required. As a result, the ultrasound operator must fight that cable torque to position and operate the probe head.

SUMMARY

In accordance with a preferred embodiment of the invention, further improvements in portable ultrasound medical imaging systems developed for use with personal computers are provided. In one embodiment the control circuitry and beamforming circuitry are localized in a hand-held probe. Such an integrated package simplifies the cable requirements of the probe, without adding significant weight to the probe.

An embodiment of the invention includes a probe having a plurality of circuit boards or circuit panels that are mounted within a generally rectangular cavity within a hand-held housing. The circuit panels each have one or more integrated circuits and are mounted in planes that are parallel to one another. These integrated circuits can be fabricated using a standard CMOS process that will support voltage levels between 5V and 200V.

A particular embodiment of the invention utilizes two or three circuit boards or panels, a center panel having a center system controller and a communication link to an external processor. The center panel can be mounted between a pair of surrounding panels, each including a memory and a beamforming circuit. The system accommodates the use of different probe elements and can employ a variable power supply that is adjusted to different levels for different probes. Also, it is desirable to use a variable clock generator so that different frequencies can be selected for different probes.

Another preferred embodiment of the invention provides a small probe that is connected by a first cable to an interface housing. The interface housing can contain the beamformer device and associated circuits and is a small light weight unit that can be held in one hand by the user while the other hand manipulates the probe. Alternatively, the interface housing can be worn on the body of the user with a strap, on the forearm or the waist with a belt, for example, or in a pocket of the user. A preferred embodiment using such an interface can include two or three circuit boards as described in greater detail herein.

In another preferred embodiment, the probe incorporating the beamformer, or the probe with the interface housing can be connected to a wearable personal computer. In this embodiment, the computer performing scan conversion, post signal processing or color doppler processing is located in a housing worn by the user, such as on the forearm, on the waist or in a pocket. A power supply board can be inserted into the probe, into the interface housing or in another external pod and can include a DC-DC converter. The display system can also include a head mounted display. A handheld controller can be connected to the computer or interface by wire or wireless connection.

A preferred embodiment of the invention can utilize certain safety features including circuits that check the power supply voltage level, that test every channel of the beamformer and assists in setting gain levels, that counts pulses per second and automatically shuts off the system to prevent over-radiating of the patient.

Another preferred embodiment of the invention employs the use of dedicated controls that the user can employ to perform specific tasks during a patient study. These controls are readily accessible and intuitive in use. These controls provide for freezing or unfreezing of the image on the display, for recording an image in electronic memory, to measure distances in two dimensions using a marker or caliper and a "set" function to fix two markers or calipers on screen, a track ball, touchpad or other manually manipulated element to control the marker, a time gain compensation control, such as 8 slide pots, to correct for sound attenuation in the body, scale or depth control to provide a zoom feature and for selection of focal zones.

The system can be employed with a number of probe system and imaging methods. These include the generation of color Doppler, power Doppler and spectral density studies. These studies can be aided by the use of contrast agents that are introduced into the body during a study to enhance the response to ultrasound signals. Such agents can also include medications that are acoustically released into the body when they are activated by specific acoustic signals generated by the probe transduce array.

BRIEF DESCRIPTION OF THE DRAWINGS

The foregoing and other objects, features and advantages of the invention will be apparent from the following more particular description of an ultrasonic probe with integrated electronics, as illustrated in the accompanying drawings in which like reference characters refer to the same parts throughout the different views. The drawings are not necessarily to scale, emphasis instead being placed upon illustrating the principles of the invention.

FIG. 4A is a block diagram of a particular 1-dimensional time-domain beam former.

DETAILED DESCRIPTION

Figure 1:
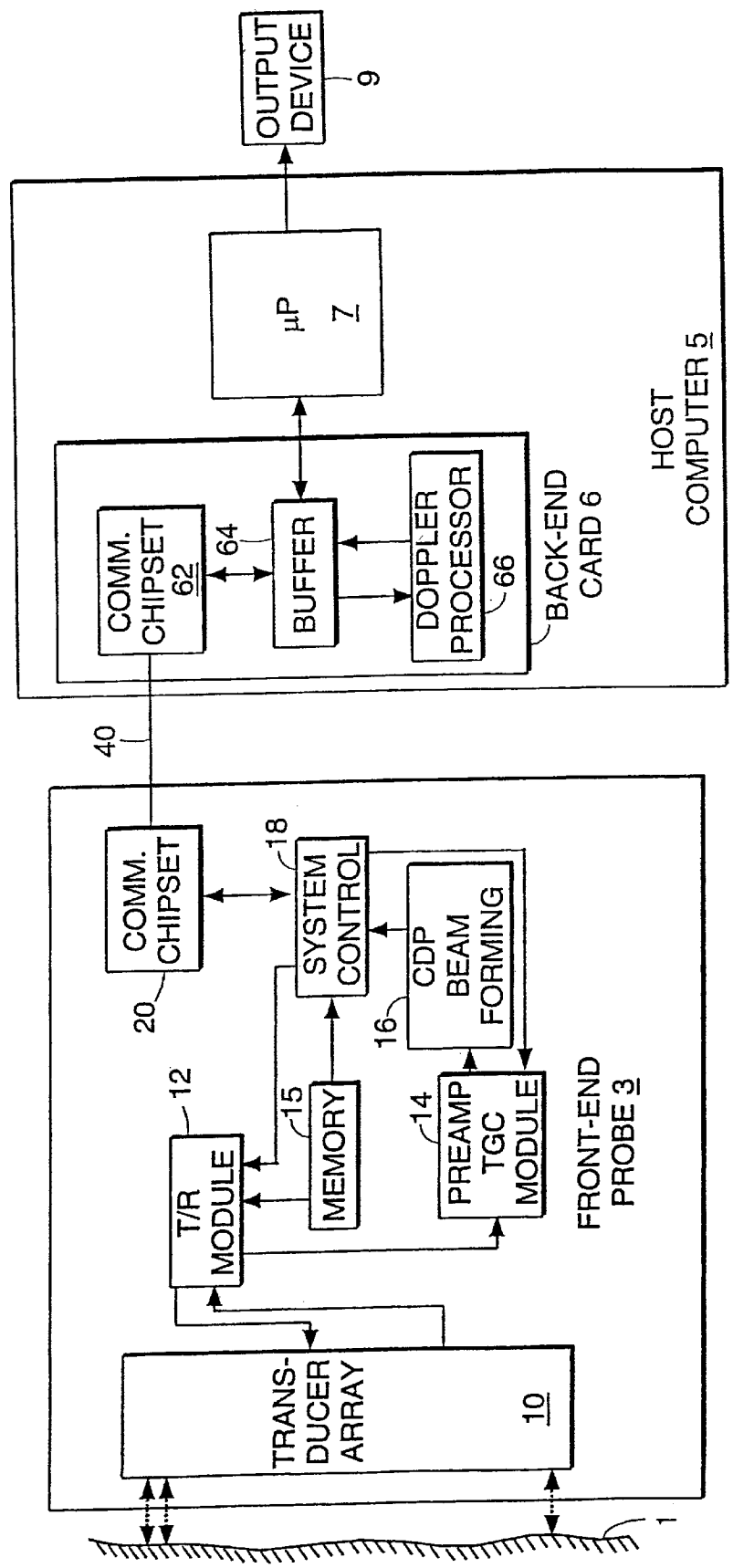
FIG. 1 is a schematic block diagram of an integrated probe system.

FIG. 1 is a schematic block diagram of an integrated probe system. Illustrated are a target object 1, a front-end probe 3, and a host computer 5. The front-end probe 3 integrates a transducer array 10 and control circuitry into a single hand-held housing. The control circuitry includes a transmit/receive module 12, a pre-amp/TGC module 14, a charge domain processor (CDP) beamforming module 16, and a system controller 18. Memory 15 stores program instructions and data. The CDP beamformer integrated circuit 16 includes a computational capacity that can be used to calculate the delay coefficients used in each channel. The probe 3 interfaces with the host computer 5 over a communications link 40, which can follow a standard high-speed communications protocol, such as the Fire Wire (IEEE 1394 Standards Serial Interface) or fast (e.g., 200 Mbits/second or faster) Universal Serial Bus (USB 2.0) protocol. The standard communication link to the personal computer operates at least at 100 Mbits/second or higher, preferably at 200 Mbits/second, 400 Mbits/second or higher. Alternatively, the link 40 can be a wireless connection such as an infrared (IR) link. The probe 3 thus includes a communications chipset 20.

The host computer 5 can include a back-end card 6, which includes a communications chipset 62, a buffer 64, and a Doppler processor 66. The back-end card 6 is controlled by a microprocessor 7 for providing output to an output device 9.

The components in the portable ultrasound system require a continuous source of data for correct operation. For instance, the beamformer 16 requires steering data, the transmit circuitry 12 requires data to instruct it where to focus the next pulse and when to fire, and the TGC 14 needs to know what gain level is appropriate at the given time. Additionally, further information may be required synchronous to the scanning operation to control how the beamformed data is sent back to the host. For instance, a DATA-VALID signal can be helpful to reduce the amount of data that the host 5 actually has to process. Along with data, the various parts of the ultrasound system relies on common synchronization for the system to work in harmony. For example, the transmitter must be fired at an exact time with respect to when the beamformer is looking at a particular position.

Engineering goals of the ultrasonic probe include small size, thermal management, low-power consumption, and the capability and flexibility to allow efficient high resolution imaging as well as calibration and experimentation. The small size and low-power operation implies dense storage. The capability and flexibility entails the ability to use irregular firing sequences, concurrent reprogramming and use for seamless adaptive beamforming modes, as well as fill flexibility to perform debugging and complete-set imaging. Ergonomic, economic portable design also requires a cost-effective, non-encumbering connection between the scan head 3 and the PC host 5. A general description of the probe system can be found in International Application PCT/US96/11166, filed on Jun. 28, 1996, now U.S. Pat. No. 5,964,709 issued on Oct. 12, 1999, which is a continuation-in-part application of U.S. Ser. No. 08/599,816 filed on Feb. 12, 1996, which is a continuation-in-part application of U.S. Ser. Nos. 08/496,804 and 08/496,805 both filed on Jun. 29, 1995, now U.S. Pat. Nos. 5,590,658 and 5,839,442, the above patents and applications being incorporated herein by reference in their entirety.

Additional factors of interest include ease, speed, and low-cost of design and manufacturing. These factors motivate the use of a Field Programmable Gate Array (FPGA) architecture. Additionally, they involve the use of a design that can be extended easily to diverse applications. However, FPGAs are severely limited in terms of operating speed, logic and storage density. This has significant ramifications.

Figure 2C:
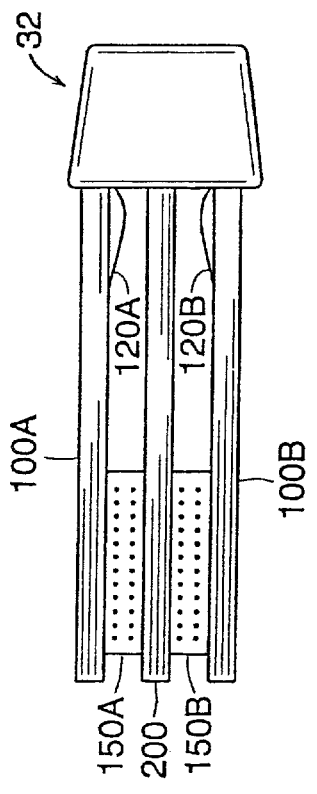
FIGS. 2A–2C illustrate a particular embodiment of packaging integrated probe electronics.
Figure 2B:
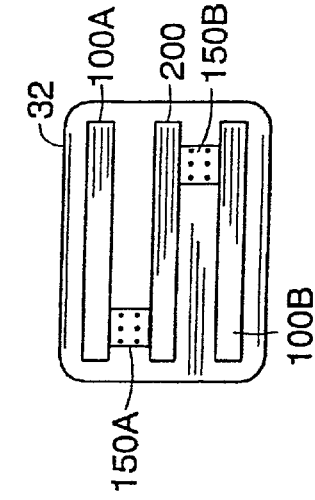
Figure 2A:
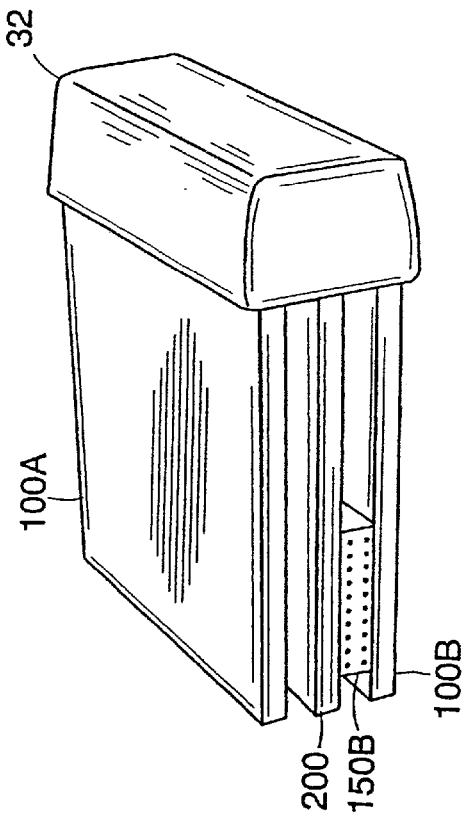

FIGS. 2A–2C illustrate a particular embodiment of integrated probe electronics. FIG. 2A is a perspective view showing a transducer array housing 32, an upper circuit board 100A, a lower circuit board 100B, and a central circuit board 200. Also shown is a lower Molex connector 150B carrying data and signal lines between a central circuit board 200 and the lower circuit board 100B. The transducer array housing 32 can be a commercially available unit having a pair of flexible cable connectors 120A, 120B (See FIG. 2C) connected to the upper board 100A and lower board 100B, respectively, with strain relief. FIG. 2B is a back-end view of the probe, which also shows an upper Molex connector 150A. FIG. 2C is a side view of the probe. Using 8 mm high Molex connectors 150A, 150B, the entire stack has a thickness of approximately 30 mm or less, with this particular embodiment being about 21 mm.

Small size is achieved through the use of modern fabrication and packaging echniques. For example, by exploiting modern semiconductor fabrication techniques, umerous circuit functions can be integrated onto single chips. Furthermore, the chips can be mounted using space-saving packaging, such as chip on-board technology. As technology improves, it is expected that the size of the electronic components will decrease further.

More functionality can be included within the handheld probe such as a wireless IEEE 1394 connection to the personal computer. A display can be mounted directly on the handheld probe, for example, to provide a more usable and user-friendly instrument.

Figure 3A:
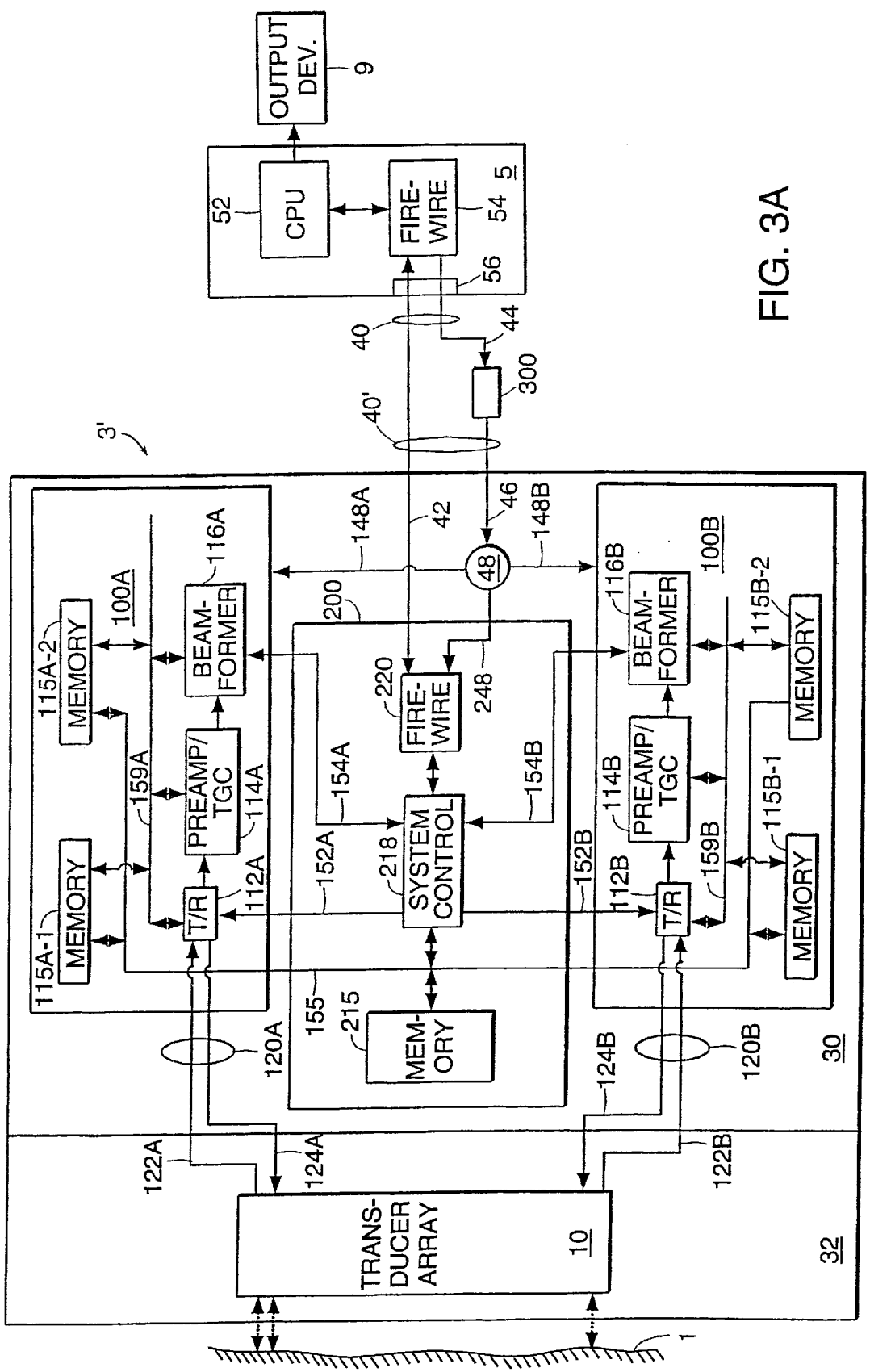
FIG. 3A is a schematic block diagram of a particular embodiment of an integrated probe system.

FIG. 3A is a schematic block diagram of a particular embodiment of an integrated probe system. The host computer 5 can be a commercially available personal computer having a microprocessor CPU 52 and a communications chipset 54. A communications cable 40 is connected through a communications port 56 to the communications chipset 54.

The front-end probe 3' includes a transducer head 32, which can be an off-the-shelf commercial product, and an ergonomic handheld housing 30. The transducer head 32 houses the transducer array 10. The housing 30 provides a thermally and electrically insulated molded plastic handle that houses the beamforming and control circuitry.

The beamforming circuitry, as shown, can be embodied in a pair of analog circuit boards 100A, 100B. Each analog circuit board 100A, 100B includes a respective transmit/receive chip 112A, 112B; a preamp/TGC chip 114A, 114B; a beamformer chip 116A, 116B; all of which are interconnected with a pair of the memory chips 115A-1, 115B-1, 115A-2, 115B-2 via an operational bus 159A, 159B. In a particular embodiment of the invention, the memory chips are Video Random Access Memory (VRAM) chips and the operational bus is 32 bits wide. Furthermore, preamp/TGC chips 114 and beamformer chips 116 operate on 32 channels simultaneously. The transmit/receive chips 112 include a 64 channel driver and a 64-to-32 demultiplexer.

FIG. 4A is a block diagram of a particular 1-dimensional time-domain beamformer. The beamformer 600 features 32-channel programmable apodized delay lines. In addition, the beamformner 600 can include an on-chip output band-pass filtering and analog-to-digital conversion.

As illustrated in FIG. 4A, the beamformer 600 includes a plurality of single channel beamforming processors 620 subscript I, . . . , 620 subscript J. Imaging signals are represented by solid leader lines, digital data is represented by dashed leader lines, and clock and control signals are illustrated by alternating dot and dash leader lines. A timing controller 610 and memory 615 interface with the single channel beamforming processors 620. Each single channel beamforming processor includes clock circuitry 623, memory and control circuitry 625, a programmable delay unit with sampling circuitry 621, in a multiplier circuit 627.

Each programmable delay unit 621 receives an imaging signal echo E from a respective transducer element. The outputs from the single channel beamforming processors 620 are added in a summer 630. An FIR filter 640 processes the resulting imaging signal, which is digitized by the analog-to-digital (A/D) converter 650. In a particular embodiment of the invention, both the FIR filter 640 and the A/D converter 650 are fabricated on chip with the beamforming processors 620.

The choice of an FPGA implementation as well as extensibility for ease of modification, points to the use of VRAMs for the memory modules. VRAM is a standard Dynamic RAM (DRAM) with an additional higher-speed serial access port. While DRAM has two basic operations e.g. read and write memory location, VRAM adds a third operation: transfer block to serial readout register. This transfers a block (typically 128 or 256 words) of data to the serial readout register which can then be clocked out at a constant rate without further tying up the DRAM core. Thus refresh, random access data read/write, and sequential readout can operate concurrently.

In the probe 3', dual-ported operation is beneficial so the data loading performed by the host 5 can be decoupled from data sent to memory modules. A modular architecture which allows additional VRAMs to be added in order to obtain additional bandwidth is useful, particularly when the exact data rate requirements may change. Using wide memories, the data does not have to be buffered before going to the various destination modules in the system. A particular embodiment uses five 256 Kword by 16 bit VRAMs which yields a total of 80 output lines. If fewer output lines are required, fewer VRAMs can be used. If more output lines are required, only very minor modifications to the controller have to be made.

The downside is that VRAM is lower density than other varieties of DRAM. Currently only 512 Kbyte VRAM chips are available. Synchronous DRAM (SDRAM) is 2 Mbyte/chip, but expects buffering of all data from the memory to the various destination modules because it is not continuous. The use of SDRAM implies that the modules accept data bursts instead of continuous data. Additionally, more buffering of host data can be used or else concurrent readout and loading may not be possible. Using a multiple data rate feature in the controller can reduce the storage requirements making VRAM a first embodiment. However, a further preferred embodiment uses SDRAM to provide further improvements in the speed and capacity of the system.

The control circuitry, as shown in FIG. 3A, is embodied in a digital circuit board 200. The digital circuit board 200 includes a Fire Wire chipset 220, a system control chip 218 to control the scan head, and a memory chip 215. In a particular embodiment of the invention, the memory chip 215 is a VRAM chip and the system control chip 218 is interconnected to the various memory chips 115, 215 over a control bus 155, which in this particular application is 16 bits wide.

As illustrated, the system control chip 218 provides scan head control signals to transmit/receive chips 112A, 112B over respective signal lines 152A, 152B. The transmit/receive chips 112A, 112B energize the transducer array 10 over transmit lines 124A, 124B. Received energy from the transducer array 10 is provided to the transmit/receive chips 112A, 112B over receive lines 122A, 122B. The received signals are provided to the pre-amp/TGC chips 114A, 114B. After being amplified, the signals are provided to the beamformer chips 116A, 116B. Control signals are exchanged between the beamformer and the system controller over signal lines 154A, 154B to adjust the scan beam.

The five VRAM chips 115A-1, 115A-2, 115B-1, 1151B-2, 215 serve to supply the real-time control data needed by the various operating modules. The term "operating modules" refers to the different parts of the system that require control data—namely the beamformers 116A, 116B, transmit/receive chips 112A, 112B, and preamp/TGC chips 114A, 114B. The system controller 218 maintains proper clocking and operation of the VRAM to assure continuous data output. Additionally, it generates clocks and control signals for the various operating modules of the system so that they know when the data present at the DRAM serial port output is for them. Finally, it also interfaces with the host (PC) 5 via a PC communications protocol (e.g., FireWire or high speed bus) to allow the host 5 to write data into the VRAM.

The system controller 218 can be consolidated into a single FPGA with an additional auxiliary FPGA used for generating the 4-phase clocks and adding the two beamformers' outputs. A Q2009 144-pin QuickLogic FPGA is a suitable choice.

Some of the VRAMs are shared by multiple modules. The 64-bit output of four VRAMs 115A-1, 115A-2, 115B-1, 115B-2 is used by both the transmit module as well as the beamformer. This is not a problem, because typically only one requires data at any given time. Additionally, the transmit module chip uses relatively less data and thus it is wasteful to have to dedicate entire VRAMs for transmit operations. In order to allow the VRAM data to be shared by multiple modules, codes are embedded in the VRAM data that the controller deciphers and asserts the appropriate MODCLOCK line.

The fifth VRAM 215 is used to generate data that is not shared by multiple modules. For example, it is convenient to put the control for the TGC here because that data is required concurrently with beamformer data. It can also be useful to have one dedicated control bit which indicates when valid data is available from the beamformer and another bit indicating frame boundaries. Thus, because the location of the data in the VRAM corresponds to the position in the frame scanning sequence, additional bits are synchronized with the operation of the system. Analog CCD clock enable signals can also be generated to gate the analog CCD clock to conserve power. Lastly, the VRAM can be used to generate test data for a D/A converter to test the analog circuitry with known waveforms.

As the system is reduced in size, the number of VRAMs may be reduced. In a SDRAM system clocked twice as fast, the four shared VRAM chips may be merged into two SDRAM chips in a 128 line system, for example.

The data sent to the beamformer and transmit modules are bit-serial within a channel, with all channels being available in parallel. Thus for the beamformer module, each bit fully specifies a single channel with two clocks being required for each delta-delta value. For the transmit module, two transmit channels share each bit line with alternating clocks strobing in data for the two channels. All per channel transmit module coefficients (such as start time) are presented bit-serially.

The data in the VRAM is organized into runs. A run consists of a one word header, which is interpreted by the VRAM controller, followed by zero or more actual data words which are used by the various modules. The headers (see Table 1) specify where the data in the run is destined, how fast it should be clocked out, and how many values there are in the run. (Note that the run destination is only for the data coming out of the 4 VRAMs. The bits coming out of the controller VRAM always have the same destinations.) The headers are also used to encode the special instructions for Jump, Pause, and End described below.

TABLE 1

VRAM Instruction Data Format (Only top VRAM matters)

Bit Position

| Command | 15 | 14 | 13 | 12 | 11 | 10 | 9 | 8 | 7 | 6 | 5 | 4 | 3 | 2 | 1 | 0 |
|---|---|---|---|---|---|---|---|---|---|---|---|---|---|---|---|---|
| Data | Mod Sel (2–7) | | | Rate | | Length | | | | | | | | | | |
| Pause | 0 | 0 | 1 | Rate (not 0 1) | | Pause Count | | | | | | | | | | |
| Wait | 0 | 0 | 1 | 0 | 1 | 0 | 0 | 0 | 0 | 0 | 0 | 0 | 0 | 0 | 0 | 1 |
| Jump | 0 | 0 | 0 | 0 | 0 | 0 | Jump Addr / 0x100 | | | | | | | | | |
| End | 0 | 0 | 0 | 0 | 0 | 1 | X | X | X | X | X | X | X | X | X | X |

The data in the VRAM are read out basically sequentially but some variations are allowed to reduce the memory requirements and facilitate system operation based on several observations about how the ultrasound system operates.

The first observation is that the peak control data rate requirements are far higher than the average rates needed. This is because, during close zone imaging, the focus may be updated at every clock to maintain maximal sharpness. However, for deep zones approaching the far field, the focusing parameters need not vary very quickly. Thus the data may be supplied at a lower rate. This is accomplished by the use of a 2-bit RATE field associated with each run (see Table 2). The RATE field allows the specified run to be clocked out at either the full system clock rate (which can be 8–32 MHZ), one-half, one-quarter, or one-eighth of that rate.

TABLE 2

Rate Field Definitions

| Rate | | | |
|---|---|---|---|
| Bit 12 | Bit 11 | Data Meaning | Pause Length |
| 0 | 0 | New Data Every Clock | PauseCount Clocks |
| 0 | 1 | New Data Every Other Clock | PauseCount*2 Clocks |
| 1 | 0 | New Data Every 4 Clocks | PauseCount*4 Clocks |
| 1 | 1 | New Data Every 8 Clocks | PauseCount*8 Clocks |

The next observation is that there are often large gaps during which time data is not required. After a transmit pulse is fired into a deep zone, a relatively large amount of time can pass before its echo is received and the beamformer is activated. Thus it is advantageous to not have to waste VRAM space for work time periods. For this reason, explicit pause commands are allowed. When the system controller 218 receives a pause command, it waits the specified number of clock cycles before reading the next word in the VRAM memory. The PAUSECOUNT is a 11 bit number which can take on the range 1–2047. This is additionally scaled by the RATE field to allow pauses of up to 16376 (2047*8) system clock cycles. Note that the RATE field can only take on the values 0, 2 and 3 because a pause of RATE 1 is interpreted as a wait command, described next. This is not a problem, however, because typically only RATE 0 is used for maximum wait accuracy (to within one clock) and RATE 3 is used for maximum wait time (up to 16376 clock cycles).

Because the data from the beamformer 116 has to be sent back to the host 5 over a bandwidth-constrained link, buffering and flow- control are required to prevent data loss. The buffering is achieved by a 16K by 18 FIFO while the flow control is achieved by feeding the FIFO fullness indication back to the system controller 218. In this way, if the FIFO becomes too full, the scanning stops until the FIFO has been emptied. However, the scanning should not stop arbitrarily because it is timed with the propagation of the sound waves. Thus explicit synchronization points can be inserted into the code, and at these points the controller waits until the FIFO is empty enough to proceed safely. The wait command is used to indicate these synchronization points. The wait command causes the controller to wait until the WAITPROCEED line is high. Currently this is connected (via the aux FPGA) to the "not half-full" indicator on the FIFO. Thus the wait commands can be placed at least every 8K data-generating cycles to assure that data overflow cannot occur. Because this is greater than one ultrasound line, it still allows multi-line interleaving to be used.

The next command is the jump command. This allows non-sequential traversal through the VRAM memory. This is employed so that the VRAM memory can be modified concurrently with the readout operation and also to make it easier to add and remove variable size control sequences. To understand why this is useful, consider the following example: Imagine that one wants to change the data in VRAM locations 512–1023 while continuing operation of the scanning using the other locations. If the host were to just modify locations 512–1023, there is no guarantee that they will not be used exactly when they are in the middle of being modified. Thus the data would be in an indeterminate state and could lead to an erroneous sequence. However, if location 512 is first modified to be a jump to location 1024, and locations to 513–1023 are then modified to their new values, and location 512 is then finally modified to its new value, this race condition cannot occur. (Assuming that it is not reading locations 513–1023 at the start of the modifications but blank regions can be left to get around this.) Additionally "subroutines" (which can only be used once per scan due to the fact that the return is coded as an absolute jump) can be used to allow easy change of the scan sequence.

A jump always takes 128 cycles to execute because the system controller has to load this new start address into the VRAMs and transfer the new row of data to the serial shift register. This typically takes only about 25 cycles, but because other parts of the system controller may have access to the VRAM (such as the refresh or host controller), a safe upper bound is used to maintain a fixed delay.

The last command is the end command. This is used at the end of the sequence for a frame to tell the system controller that the frame has completed. The controller then stops fetching instructions until it is restarted (from location 0) by host if it is in single-frame mode. If it is in continuous mode then it will start immediately on the next frame. (After 128 cycles required for the implied jump 0).

Figure 5A:
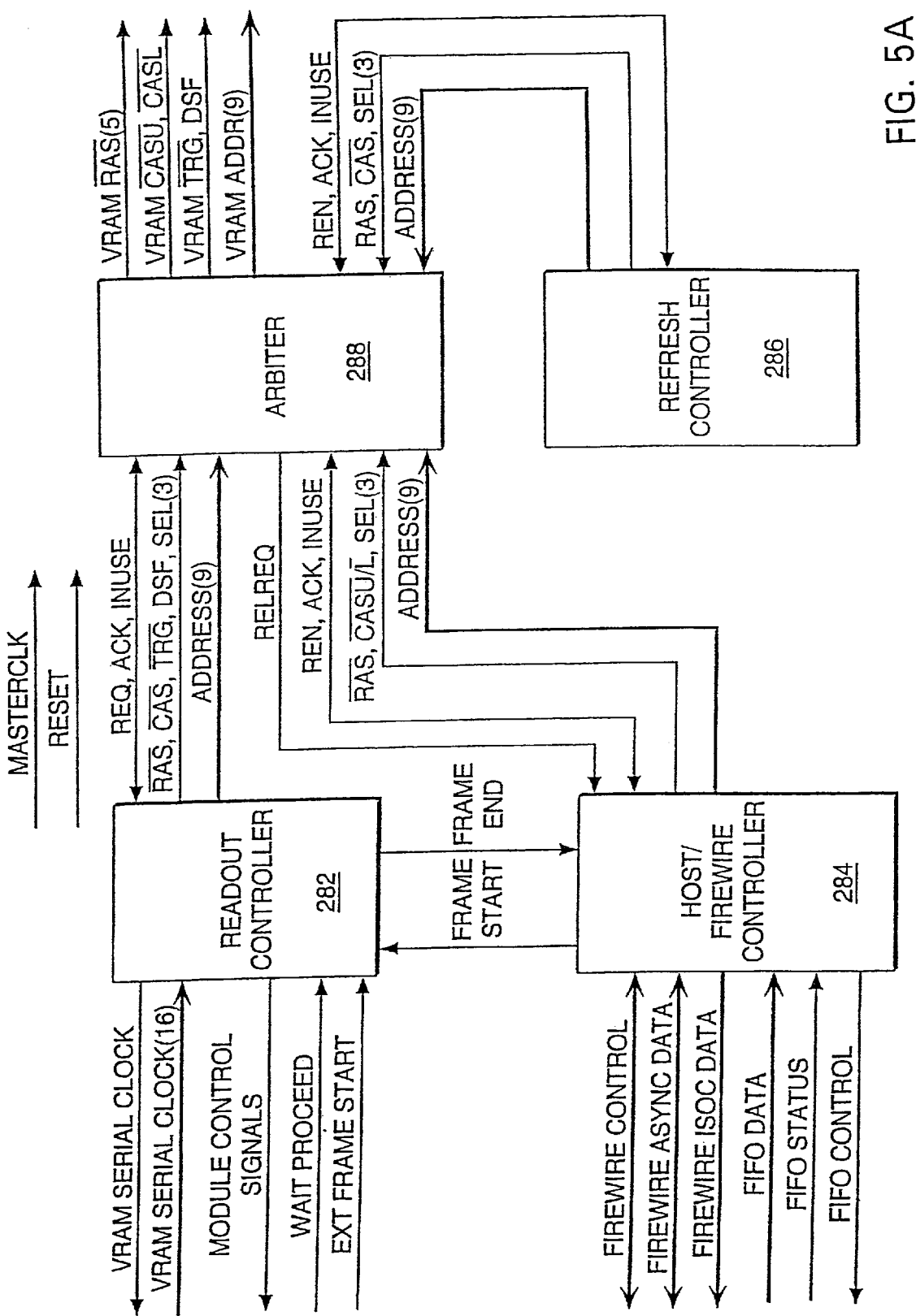
FIG. 5A is a functional block diagram of the system controller of FIG. 3.

FIG. 5A is a functional block diagram of the architecture of the system controller of FIG. 3A. The system controller 218 has four basic parts: a readout controller 282, a host controller 284, the refresh controller 286, and the Arbiter 288. The first three support the three basic operations on the VRAM: reading out data, writing in of data at host's request, and refreshing the DRAM core. The arbiter 288 is responsible for merging the requests of the first three sections into one connection to the VRAM's DRAM core. Only one of the first three sections can have control at a given time, so the explicitly request control and wait until this request is acknowledged by the arbiter 288. They also must tell the arbiter 288 when they are still using the DRAM so that the arbiter knows not to grant it to one of the other sections. This is done via the INUSE lines.

Additionally the arbiter 288 sends the host controller 284 a RELREQ or relinquish request signal to ask the host controller 284 to give up ownership of the DRAM core because some other section wants it. Note that only the host 284 controller needs to be asked to relinquish the bus because the readout controller 284 and refresh controller 286 both only use the DRAM core for fixed short intervals. The host controller 284, however, can hold on to the DRAM as long as there is data coming over the FireWire to be written into the DRAM, so it needs to be told when to temporarily stop transferring data.

Note that the serial section of the VRAMs is not multiplexed -it is always controlled by the readout controller 282. The VRAM serial data also only goes to the readout controller 282.

The readout controller 282 controls the sequencing of the data out the VRAMs' serial access ports. This involves parsing the data headers to determine what locations should be read, clocking the VRAM Serial Clock at the correct time, driving the module control lines, and also arranging for the proper data from the VRAM's DRAM core to be transferred into the serial access memory.

The host controller 284 is the part of the VRAM Controller that interfaces to the host 5 via FireWire to allow the host to write into the VRAM. When the host wants to write into the VRAM, it sends asynchronous packets specifying which VRAM and which addresses to modify as well as the new data to write. The host controller 284 then asks the arbiter 288 for access to the VRAM. When the DRAM core is not in use by either the readout 282 or refresh 286 controller, the arbiter 288 grants control to the host controller 284. The host controller 284 then takes care of address and control signal generation. When the whole packet has been decoded, the host controller 284 releases its request line giving up the DRAM control, allowing the other two sections to use it.

The refresh controller 286 is responsible for periodically generating refresh cycles to keep the DRAM core of the VRAM from losing its data. The refresh controller 286 has its own counter to keep track of when it needs to request a refresh. Once it gains access to the VRAMs via the arbiter 288, it generates one refresh cycle for each of the VRAMs sequentially. This reduces the amount of spikes on the DRAM power supply lines as compared to refreshing all 5 VRAMs in parallel.

The REFRATE inputs control how many system clock cycles occur between refresh cycles. (See Table 3.) This compensates for different system clock rates. Additionally, refresh may be disabled for debugging purposes.

TABLE 3

Refresh Rate Definitions

| RefRate1 | RefRate0 | System clock cycles between refresh cycles | Minimum System Clock to achieve 16 μs refresh rate |
| --- | --- | --- | --- |
| 0 | 0 | 128 | 8 MHZ |
| 0 | 1 | 256 | 16 MHZ |
| 1 | 0 | 512 | 32 MHZ |
| 1 | 1 | No Refresh | ∞ |

The arbiter controls 288 the access to the VRAM by the Readout, Host, and Refresh Controller 282, 284, 286 sections. Only one section may have access to the DRAM port of the VRAM at any given time. The arbiter 288 does not reassign control of the VRAM to another section until the section with control relinquishes it by de-asserting its IN_USE line. The sections are prioritized with the Readout Controller 282 getting the highest priority and the host controller 284 getting the lowest priority. The reasoning is that if the readout controller 282 needs access to the VRAM, but does not get it, then the system may break down as the serial output data will be incorrect. The refresh controller 286 can tolerate occasional delay, although it should not happen much. Finally, the host controller 284 can potentially tolerate very long delays because the host can be kept waiting without too many consequences except that the writing of the VRAM may take longer.

A highly capable, yet cost-effective and physically non-encumbering connection between the scan head and host computer is possible using the FireWire standard (also known as IEEE 1394). The FireWire standard is used for multimedia equipment and allows 100–200 Mbps and preferably in the range of 400–800 Mbps operation over an inexpensive 6 wire cable. Power is also provided on two of the six wires so that the FireWire cable is the only necessary electrical connection to the probe head. A power source such as a battery or IEEE1394 hub can be used. The FireWire protocol provides both isochronous communication for transferring high-rate, low-latency video data as well as asynchronous, reliable communication that can be used for configuration and control of the peripherals as well as obtaining status information from them. Several chipsets are available to interface custom systems to the FireWire bus. Additionally, PCI-to-FireWire chipsets and boards are currently available to complete the other end of the head-to-host connection. CardBus-to-FireWire boards can also be used.

Although the VRAM controller directly controls the ultrasound scan head, higher level control, initialization, and data processing and display comes from a general purpose host such as a desktop PC, laptop, or palmtop computer. The display can include a touchscreen capability. The host writes the VRAM data via the VRAM Controller. This is performed both at initialization as well as whenever any parameters change (such as number or positions of zones, or types of scan head) requiring a different scanning pattern. During routine operation when data is just being continually read from the scan head with the same scanning parameters, the host need not write to the VRAM. Because the VRAM controller also tracks where in the scan pattern it is, it can perform the packetization to mark frame boundaries in the data that goes back to the host. The control of additional functions such as power-down modes and querying of buttons or dial on the head can also be performed via the FireWire connection.

Although FireWire chipsets manage electrical and low-level protocol interface to the FireWire interface, the system controller has to manage the interface to the FireWire chipset as well as handling higher level FireWire protocol issues such as decoding asynchronous packets and keeping frames from spanning isochronous packet boundaries.

Asynchronous data transfer occurs at anytime and is asynchronous with respect to the image data. Asynchronous data transfers take the form of a write or read request from one node to another. The writes and reads are to a specific range of locations in the target node's address space. The address space can be 48 bits. The individual asynchronous packet lengths are limited to 1024 bytes for 200 Mbps operation. Both reads and writes are supported by the system controller. Asynchronous writes are used to allow the host to modify the VRAM data as well as a control word in the controller which can alter the operation mode. Asynchronous reads are used to query a configuration ROM (in the system controller FPGA) and can also be used to query external registers or I/O such as a "pause" button. The configuration ROMs contain a querible "unique ID" which can be used to differentiate the probe heads as well as allow node-lockings of certain software features based on a key.

Using isochronous transfers, a node reserves a specified amount of bandwidth, and it gets guaranteed low-overhead bursts of link access every ⅛₀₀₀ second. All image data from the head to the host is sent via isochronous packets. The FireWire protocol allows for some packet-level synchronization and additional synchronization is built into the system controller.

The asynchronous write request packets are sent from the host to the probehead in order to:

a) Configure the Link Layer controller chip (TI GPLynx or TI GP2 Lynx)

b) Control the system controller FPGA c) Write sequencing data into the VRAM

Both the "Asynchronous Write Request with Block Payload" or the "Asynchronous Write Request with Quadlet Payload" forms can be used. The later simply restricts the payload to one quadlet (4 bytes). The formats of the two packets are shown in Table 4 and Table 5. Note that these are how the packets are passed on by the TI LINK controller chip. The difference between this and the format over the wire is that the CRCs are stripped and the speed code (spd) and acknowledgment code (ackSent) are appended to the end. The Adaptec API and device driver take care of assembling the packets.

TABLE 4

Asynchronous Write Request with Quadlet Payload as Delivered by TI LINK chip

| Word | Bit (bit 0 is MSB) | | | | | | | | | | | | | | | |
|---|---|---|---|---|---|---|---|---|---|---|---|---|---|---|---|---|
| | 0 | 1 | 2 | 3 | 4 | 5 | 6 | 7 | 8 | 9 | 10 | 11 | 12 | 13 | 14 | 15 |
| 0 | | | | | | | | destinationID | | | | | | | | |
| 1 | | | | | | | | sourceID | | | | | | | | |
| 2 | | | | | | | | destinationOffsetLo | | | | | | | | |
| 3 | Data 0 | | | | | | | | | | | Data 1 | | | | |
| 4 | | | | | | | | | | | | | | | | spd |

TABLE 4-continued

Asynchronous Write Request with Quadlet Payload as Delivered by TI LINK chip

| Word | Bit (bit 0 is MSB) | | | | | | | | | | | | | | | |
|---|---|---|---|---|---|---|---|---|---|---|---|---|---|---|---|---|
| | 16 | 17 | 18 | 19 | 20 | 21 | 22 | 23 | 24 | 25 | 26 | 27 | 28 | 29 | 30 | 31 |
| 0 | | tLabel | | | | | rt | | | | tCode=0 | | | priority | | |
| 1 | | | | | | | destinationOffsetHi | | | | | | | | | |
| 2 | | | | | | | destinationOffsetLo | | | | | | | | | |
| 3 | | | | Data 2 | | | | | | | | | Data 3 | | | |
| 4 | | | | | | | | | | | | | | | | ackSent |

TABLE 5

Asynchronous Write Request with Block Payload as Delivered by TI LINK chip

| Word | Bit (bit 0 is MSB) | | | | | | | | | | | | | | | |
|---|---|---|---|---|---|---|---|---|---|---|---|---|---|---|---|---|
| | 0 | 1 | 2 | 3 | 4 | 5 | 6 | 7 | 8 | 9 | 10 | 11 | 12 | 13 | 14 | 15 |
| 0 | | | | | | | | destinationID | | | | | | | | |
| 1 | | | | | | | | sourceID | | | | | | | | |
| 2 | | | | | | | | destinationOffsetLo | | | | | | | | |
| 3 | | | | | | | | dataLength (in bytes) | | | | | | | | |
| 4 | | | | Data 0 | | | | | | | | | Data 1 | | | |
| 5 | | | | Data 4 | | | | | | | | | Data 5 | | | |
| ... | | | | ... | | | | | | | | | ... | | | |
| 3+N/4 | | | | Data N-4 | | | | | | | | | Data N-3 | | | |
| 4 | | | | | | | | | | | | | | | | spd |
| | 16 | 17 | 18 | 19 | 20 | 21 | 22 | 23 | 24 | 25 | 26 | 27 | 28 | 29 | 30 | 31 |
| 0 | | tLabel | | | | | rt | | | | tCode=1 | | | priority | | |
| 1 | | | | | | | destinationOffsetHi | | | | | | | | | |
| 2 | | | | | | | destinationOffsetLo | | | | | | | | | |
| 3 | | | | | | | extendedTcode | | | | | | | | | |
| 4 | | | | Data 2 | | | | | | | | | Data 3 | | | |
| 5 | | | | Data 6 | | | | | | | | | Data 7 | | | |
| ... | | | | ... | | | | | | | | | ... | | | |
| 3+N/4 | | | | Data N-2 | | | | | | | | | Data N-1 | | | |
| 4 | | | | | | | | | | | | | | | | ackSent |

The destination ID field holds the node ID of the destination which is the probe head FireWire controller. The physical layer chip can use this to determine if the packet is for it. The system controller can ignore this field. The tLabel field is used to match requests and responses. For write requests, this does not matter and can be ignored. The rt is the retry code used at link and/or phy level. It is not used by the system controller. The tCode field is the transaction code which determines what type of packet it is. In particular 0 is for quadlet write requests and 1 is for block write requests. The system controller parses this field to determine what type of packet it is. Currently only tCode values of 0 and 1 are recognized. The priority field is used by the PHY chip only and is ignored by the system controller. It is used in, i.e. in selecting which unit on the interface is to receive a particular packet of data.

Next, the destinationOffsetHi and destinationOffsetLo fields form the 48 bit destination start address. This indicates within the node what the data should be used for. The system controller used the destinationOffsetHi to determine the function as shown in Table 6. Note that only the 3 least significant bits of the destinationOffsetHi field are currently examined. The spd field indicates the speed at which the data was sent while the ackSent field is used to indicate status by saying how the LINK chip acknowledged the packet.

TABLE 6 destinationOffsetHi values

| destinationOffsetHi | Meaning |
|---|---|
| 0 | Write VRAM 0 |
| 1 | Write VRAM 1 |
| 2 | Write VRAM 2 |
| 3 | Write VRAM 3 |
| 4 | Write VRAM 4 |
| 5 | Write ISO Packet Length Register |
| 6 | Write System Controller Mode Word |
| 7 | Wrote to LINK chip |

As can be seen, destinationOffsetHi values of 0–4 correspond to writing the VRAMs. In this case the destination OffsetLow is set to the byte address to start writing. This is twice the standard VRAM address which is typically formed in 16-bit words. Note also that the start address (destinationOffsetLow) and the length (dataLength) can both be multiples of 4 such that all operations are quadlet aligned. The payload data is little endian and thus need not be converted if written by an Intel PC host. The length (dataLength) must additionally be between 4 and 128 bytes due to the size of the GPLynx FIFO. The total FIFO size is 200 bytes, but 72 bytes are dedicated to the asynchronous transmit FIFO required for read responses.

A destinationOffsetHi value of 5 signifies that the system controller ISO Packet Length register is to be written. The ISO Packet Length has to be set in the controller to allow it to correctly format the ISO packets back to the host via firewire. An explicit counter in the system controller is used due to the fact that the TI GPLynx chip does not assert the end-of-packet indication until one word too late. Note that the ISO Packet length also has to be set in the LNK chip. The value written is the number of 16-bit words in the ISO Packet length which also has to be set in the LNK chip. The value written is the number of 16-bit words in the ISO packet (i.e. bytes/2) and it is written in little endian order because it is only interpreted by system controller and not the LINK chip.

Specifying a destinationOffsetHi value of 6 signifies that the system controller mode word is to be modified. Currently only the least significant 16 bits are used out of each quadlet and all quadlets go to the same place so writing multiple values just causes the system controller mode word to be rewritten. Please note that the payload data is again little endian. (Putting these two facts together yields that the first two out of every four bytes are used and the second two are ignored.) The definition of the system controller Mode Word is given in Table 7.

TABLE 8

Use of AbortFrame, SingleFrame, and Run bits in System Controller Mode Word

| Abort Frame | Single Frame | Run | Meaning |
|---|---|---|---|
| 1 | 0 | 0 | Abort any current frame and wait |
| 0 | 1 | 0 | Start a single new frame |
| 0 | 0 | 1 | Keep scanning new frames |
| 0 | 0 | 0 | Let any current frame complete |

The DataLoopback bit is used to control whether the data that is read back from the host comes from A/D or from one of the VRAMs. (Currently this is VRAM 1.) This second option can be used for test purposes to test the digital data generation and collection without testing the beamformer and A/D conversion. A 0 in the DataLoopback bit indicates normal operation of reading from A/D while a 1 means that it should get data from the VRAM.

The Extra1 and Extra2 bits are available for general use. They are latched by the system controller and currently brought out on pins called EXTRA CLOCK0 and EXTRA-CLOCK1 but can be used for any purpose.

Finally setting destinationOffsetHi to 7 indicates that the data in the asynchronous packet be written back to the FireWire Link chip. This allows any of the TI TSB12LV31's (or 32's) registers to be modified by the host. This can be used to configure and enable the Isochronous data transmit. The destinationOffsetLow specifies the first register to write. Because the registers are all 4-bytes in size and must be written in their entirety, destinationOffsetLow and dataLength must both be multiples of 4. Multiple consecutive registers can be written with a single packet. Note that the data is big-endian because the TSB12V31 is designed as big-endian. This byte-swapping must be performed by the Intel PC host.

TABLE 7

System Controller Mode Word

Bit (bit 31 is MSB)

| 31–36 | 15–8 | 7 | 6 | 5 | 4 | 3 | 2 | 1 | 0 |
|---|---|---|---|---|---|---|---|---|---|
| unused | BOF Word | unused | unused | Abort Frame | Single Frame | Run | Extra2 | Extra1 | Data Loop-back |

The BOF Word field is used to set the value that the system controller will put in the high byte of the first word of an isochronous packet to indicate the beginning of frame. The BOF word field can be set to some value that is not likely to occur in typical data. This not crucial, however, because choosing a BOF word that occurs in the data will make it more likely to miss incorrect frame synchronization but will never cause false alarms where it thinks it is mis-synchronized but is really correctly synchronized. The initial value upon reset is 80 hex.

The AbortFrame, SingleFrame, and Run bits are used to control the system operation. Their use is shown in Table 8. The data FIFO is never allowed to fully empty so an entire frame cannot be read out until part of the next one is in the queue.

Read request packets are used to asynchronously read data from the probehead. This currently only consists of configuration ROM data (see below) but can be easily used for other types of data such as status information or button indications.

The Adaptec device drivers send Asynchronous Read Requests in response to explicit application requests as well as to interrogate the node's FireWire configuration ROM in response to a SendPAPICommand of P_GET_DEV_INFO or after a bus reset or when an application tries to obtain a handle to a node.

Asynchronous read requests can either be of the quadlet or block variety as with the asynchronous write requests. The formats are shown in Table 9 and Table 10. They are similar to the write request formats.

TABLE 9

Asynchronous Read Request with Quadlet Payload as
Delivered by TI LINK chip

| Word | Bit (bit 0 is MSB) |
|---|---|

| Word | 0 | 1 | 2 | 3 | 4 | 5 | 6 | 7 | 8 | 9 | 10 | 11 | 12 | 13 | 14 | 15 |
|---|---|---|---|---|---|---|---|---|---|---|---|---|---|---|---|---|
| 0 | | | | | | | | destinationID | | | | | | | | |
| 1 | | | | | | | | sourceID | | | | | | | | |
| 2 | | | | | | | | destinationOffsetLo | | | | | | | | |
| 3 | | | | | | | | | | | | | | | | spd |

| | 16 | 17 | 18 | 19 | 20 | 21 | 22 | 23 | 24 | 25 | 26 | 27 | 28 | 29 | 30 | 31 |
|---|---|---|---|---|---|---|---|---|---|---|---|---|---|---|---|---|
| 0 | | | tLabel | | | | | rt | | tCode=4 | | | | priority | | |
| 1 | | | | | | | | destinationOffsetHi | | | | | | | | |
| 2 | | | | | | | | destinationOffsetLo | | | | | | | | |
| 3 | | | | | | | | | | | | | | ackSent | | |

TABLE 10

Asynchronous Read Request with Quadlet Payload as
Delivered by TI LINK chip

| Word | Bit (bit 0 is MSB) |
|---|---|

| Word | 0 | 1 | 2 | 3 | 4 | 5 | 6 | 7 | 8 | 9 | 10 | 11 | 12 | 13 | 14 | 15 |
|---|---|---|---|---|---|---|---|---|---|---|---|---|---|---|---|---|
| 0 | | | | | | | | destinationID | | | | | | | | |
| 1 | | | | | | | | sourceID | | | | | | | | |
| 2 | | | | | | | | destinationOffsetLo | | | | | | | | |
| 3 | | | | | | | | dataLength (in bytes) | | | | | | | | |
| 4 | | | | | | | | | | | | | | | | spd |

| | 16 | 17 | 18 | 19 | 20 | 21 | 22 | 23 | 24 | 25 | 26 | 27 | 28 | 29 | 30 | 31 |
|---|---|---|---|---|---|---|---|---|---|---|---|---|---|---|---|---|
| 0 | | | tLabel | | | | | rt | | tCode=5 | | | | priority | | |
| 1 | | | | | | | | destinationOffsetHi | | | | | | | | |
| 2 | | | | | | | | destinationOffsetLo | | | | | | | | |
| 3 | | | | | | | | extendedTcode | | | | | | | | |
| 4 | | | | | | | | | | | | | | ackSent | | |

As with the asynchronous write packets, the destinationOffsetHi and destinationOffsetLow determine what is being requested. The high addresses are defined for use as Control and Status Registers and the configuration ROM while the lower address are for more general purpose use. In particular, the FireWire configuration ROM starts at destinationOffsetHi=0xffff, and destinationOffsetLow= 0xf0000400, for example.

When the system controller receives a Quadlet or Block Read Request packet from the TI LINK chip's General Receive FIFO, it formulates a Quadlet or Block Read Response packet and places it in the LINK chip's Asynchronous Transmit FIFO. The format of these packets (as placed in the Asynchronous Transmit FIFO) is shown in Table 11 and Table 12.

TABLE 11

Asynchronous Read Response with Quadlet Payload as
Expected by TI LINK chip

| Word | Bit (bit 0 is MSB) |
|---|---|

| Word | 0 | 1 | 2 | 3 | 4 | 5 | 6 | 7 | 8 | 9 | 10 | 11 | 12 | 13 | 14 | 15 |
|---|---|---|---|---|---|---|---|---|---|---|---|---|---|---|---|---|
| 0 | | | | | | | | | | | | | | | | spd |
| 1d | | | | | | | | destinationID | | | | | | | | |
| 2 | | | | | | | | reserved = 0 | | | | | | | | |
| 3 | | | | | Data 0 | | | | | | | | Data 1 | | | |

| | 16 | 17 | 18 | 19 | 20 | 21 | 22 | 23 | 24 | 25 | 26 | 27 | 28 | 29 | 30 | 31 |
|---|---|---|---|---|---|---|---|---|---|---|---|---|---|---|---|---|
| 0 | | | tLabel | | | | | rt | | tCode=6 | | | | priority | | |
| 1d | | rCode | | | | | | reserved = 0 | | | | | | | | |
| 2 | | | | | | | | reserved = 0 | | | | | | | | |
| 3 | | | | | Data 2 | | | | | | | | Data 3 | | | |

TABLE 12

Asynchronous Read Response with Block Payload as Expected by TI LINK chip

| Word | Bit (bit 0 is MSB) | | | | | | | | | | | | | | | |
|---|---|---|---|---|---|---|---|---|---|---|---|---|---|---|---|---|
| | 0 | 1 | 2 | 3 | 4 | 5 | 6 | 7 | 8 | 9 | 10 | 11 | 12 | 13 | 14 | 15 |
| 0 | | | | | | | | | | | | | | | spd | |
| 1 | | | | | | | destinationID | | | | | | | | | |
| 2 | | | | | | | reserved = 0 | | | | | | | | | |
| 3 | | | | | | | dataLength (in bytes) | | | | | | | | | |
| 4 | | | | | Data 0 | | | | | | | | Data 1 | | | |
| 5 | | | | | Data 4 | | | | | | | | Data 5 | | | |
| ... | | | | | ... | | | | | | | | ... | | | |
| 3+N/4 | | | | | Data N-4 | | | | | | | | Data N-3 | | | |
| | 16 | 17 | 18 | 19 | 20 | 21 | 22 | 23 | 24 | 25 | 26 | 27 | 28 | 29 | 30 | 31 |
| 0 | | | tLabel | | | | rt | | tCode=7 | | | | priority | | | |
| 1 | | rCode | | | | | reserved = 0 | | | | | | | | | |
| 2 | | | | | | | reserved = 0 | | | | | | | | | |
| 3 | | | | | | | extendedTcode = 0 | | | | | | | | | |
| 4 | | | | | Data 2 | | | | | | | | Data 3 | | | |
| 5 | | | | | Data 6 | | | | | | | | Data 7 | | | |
| ... | | | | | ... | | | | | | | | ... | | | |
| 3+N/4 | | | | | Data N-2 | | | | | | | | Data N-1 | | | |

The spd, tLabel, rt, and priority values are copied from the request packet. The destinationID is taken from the sourceID of the request packet. Note that all packet CRCs are generated by the TI LINK chip and are thus note included the data that the system controller must generate. (The ROM CRCs do have to be computed explicitly off-line.)

The rCode field is used to indicate the status of the reply. In particular, 0 means resp_complete indicating all is well. A value of 6 means resp_type_error indicating that some field of the packet was invalid or unsupported. In this case, if the request was a block request then the dataLength of the response packet must be 0 and no data should be included. A resp_type_error is returned if the dataLength or destinationOffsetLow of the request packet were not multiples of 4 or if the dataLength was not between 4 and 32 (for block packets). This is because the TI chip's asynchronous transmit FIFO is configured to be 12 quadlets (for 8 payload quadlets+4 quadlet header) so that the receive FIFO can be 36 quadlets in order to allow 128 byte payload write packets. The longest request the Adaptec device drivers should request is 8 quadlets because that is the length of the configuration ROM. In any case, it is assumed that if a long transfer failed, it falls back to a smaller request.

The FireWire specification expects each FireWire node to have a configuration ROM that contains various details about the device, its requirements, and its capabilities. This ROM is to be queried via Read Request packets. There are two types of ROM implementations: a minimal ROM and a general ROM. The former has only one quadlet (4-byte) piece of data indicating a 24-bit vendor ID. The general ROM has many other fields, and many which are optional ranging from the ASCII name of the vendor and device to its power consumption and how to access its capabilities.

One of the required fields in a general ROM is a node unique ID. This consists of the 24-bit vendor ID and a 40-bit chip ID. The 40-bit chip-ID is up to the vendor to assign such that all nodes have unique values. The node unique ID's are required to keep a consistent handle on the device if the FireWire bus is reset or reconfigured during operation. When a device is first opened, the application reads its configuration ROM and determines if it wants to work with it. If so it records its node unique ID and opens a connection to the device via that node unique ID. This is then at any given time mapped to its FireWire ID (16-bit) by the host adapter and its device driver. If the topology changes or a FireWire bus reset occurs, the node's FireWire ID can change, however the node unique ID will not. Thus, in such an event, the adapter automatically determines the new FireWire ID and continues. Thus for smooth operation, particularly with multiple heads attached to the system, implementing node unique IDs and the configuration ROM is required.

The configuration ROM is divided into several sections. The sections of lar interest are the first word, which defines the length and CRC of the ROM, the words comprising the Bus_Info_Block, which gives some fixed 1 394-specific ation (such as Node Unique ID), and the last 3 words representing the Root ory which is a set of key-value tagged entries. Only the two required key-value are included the ROM built into the FPGA. An 8-word ROM that can be used is in Table 13.

TABLE 13

FireWire Configuration ROM built into FPGA

| Word | Bit (bit 0 is MSB) | | | | | | | | | | | | | | | |
|---|---|---|---|---|---|---|---|---|---|---|---|---|---|---|---|---|
| | 0 | 1 | 2 | 3 | 4 | 5 | 6 | 7 | 8 | 9 | 10 | 11 | 12 | 13 | 14 | 15 |
| 0 | info_length=0x04 | | | | | | | | | | crc_length=0x07 | | | | | |
| 1 | 0x31 ("1") | | | | | | | | | | 0x33 ("3") | | | | | |
| 2 | bits=0x2 | | | | reserve=0 | | | | | | cyc_clk_acc=0xff | | | | | |
| 3 | node_vendor_id=1234567 (ox12d687) | | | | | | | | | | | | | | | |
| 4 | chip_id_lo=890 (0x0000037a) | | | | | | | | | | | | | | | |
| 5 | Root_Dir_Len=0x0002 | | | | | | | | | | | | | | | |
| 6 | ModVendIDKey=0x03 | | | | | | | | | | module_vendor_id=1234567 (0x12d687) | | | | | |
| 7 | NodeCapKey=0x0c | | | | | | | | | | node_capabilities=0x000000 | | | | | |

| Word | 16 | 17 | 18 | 19 | 20 | 21 | 22 | 23 | 24 | 25 | 26 | 27 | 28 | 29 | 30 | 31 |
|---|---|---|---|---|---|---|---|---|---|---|---|---|---|---|---|---|
| 0 | rom_crc_value=0xfbc8 | | | | | | | | | | | | | | | |
| 1 | 0x39 ("9") | | | | | | | | | | 0x34 ("4") | | | | | |
| 2 | max_rec=6 | | | | | | | | | | reserve=0x000 | | | | | |
| 3 | node_vendor_id=1234567 (ox12d687) | | | | | | | | | | chip_is_hi=0 | | | | | |
| 4 | chip_id_lo=890 (0x0000037a) | | | | | | | | | | | | | | | |
| 5 | Root_Dir_CRC=0xbc8e | | | | | | | | | | | | | | | |
| 6 | module_vendor_id=1234567 (0x12d687) | | | | | | | | | | | | | | | |
| 7 | node_capabilities=0x000000 | | | | | | | | | | | | | | | |

Isochronous packets are used for the probehead-to-host communication of formed data. This is conceptually a stream of 16-bit numbers punctuated by frame markers. The frame markers are important to keep in sync with where in the frame the corresponds. While some ultrasound systems use elaborate frame and line markers added in the data, the integrated system can use a single auxiliary bit, which is not sent as part of the data, to mark frame boundaries. Line boundaries can be derived by knowing the VRAM sequencing program.

While asynchronous packets can be sent at will and do not have any guarantee of width availability, isochronous packets can be used as low-overhead way to send a anteed rate of data. Once a peripheral reserves a specified amount of bandwidth, it gets guaranteed bursts of link access every 1/8000 second. All data from the head to the host is sent via isochronous packets. Because isochronous packets are limited to 1/8000 second, this is a frame of data. The FireWire specification describes the use of synchronization bits which can be used to tag each isochronous packet with a 4 bit SYNC code. The Adaptec FireWire-to-PCI bridge can then use the Sync field to assure proper frame alignment. However, the TI GPLynx Controller chip only supports frame-level granularity of when to send packets and not packet level so when the System Controller tells the FireWire link chip it has data, it must be prepared to send a whole frame of data. Because the FIFO is much smaller than a frame, a sage option is to reduce the effective FireWire frame size to one packet. Then a specific Beginning of Frame (BOF) code in the high byte of the first word of every ultrasound frame and force the start of ultrasound frames to occur at the beginning of FireWire frames (and packets) and do frame-level synchronization in the Ultrasound application software. For efficiency, a full ultrasound frame of data can still be read in one FireWire call (and hence one interrupt).

There are three steps in setting up for Isochronous head-to-host data transfers. These initialization steps need only be performed once per probe initialization.

The first step is to reserve isochronous bandwidth. This reservation causes a central record of the request (in the FireWire isochronous cycle manager node) to be kept to assure that the total bandwidth allocated does not exceed the total bandwidth of the link. For example, this reservation is achieved using the Adaptec API BusConfig 0 command with Cmd field set to P_ALLOCATE_RESOURCE. A requested payload in bytes is passed in. This can be the amount of data desired in every 1/8000 second. Setting this value too high simply wastes reserved bandwidth on the FireWire interface which is not a problem if there is only one device. Setting this value too low may constrain the head-to-host data rate. No overflows or data loss are likely to occur, the scanning may simply proceed slower. The resource allocation call will return both an isochronous channel number as well as the payload size granted. This payload size granted may be less than that requested if part of the link has already been reserved.

The next step is to set the system controller ISO packet length word to tell how long of an ISO packet to expect.

The final step is to initialize the probehead LNK chip. This is done via the writeback to LINK chip asynchronous packets described above. In particular, initializing registers 54h, 58h, and 5ch is necessary. The probehead can then be told to start sequencing and the data will flow back.

If multiple probes are connected to the system then the isochronous bandwidth reservation can take place once but at any given time, only one probe's isochronous transmission (as well as its sequencing) is enabled.

As previously described, isochronous data transfers are used to deliver the probe head data to the host. Maintaining frame synchronization is necessary. The FireWire will support sub-frame packetization of about 3000 bytes but it is up to the system controller to implement frame synchronization on top of this. Synchronization is achieved via two methods:

1. The high byte of the first word in the first packet of a frame is set to the Beginning of Frame (BOF) code. (This can be set in the system controller Mode word).
2. All frames are padded to consume a whole number of packets.

When these two are combined, they guarantee that frame synchronization will be maintained if the correct number of packets are read at a time and the resynchronization can be effected by just scanning the high-byte of the first word of each packet in the data stream.

An example packetization is shown in Table 14. This depicts 4 packets of 4 words (8 bytes) apiece showing one complete ultrasound frame and the first packet of the next frame. The ultrasound frame size is 10 words. As can be seen, the Hi byte of the first word is set to the BOF code. This can be examined to assure that proper synchronization has been maintained. The data is then split into the three packets 1–3. Because the frame ends in the middle of packet 3, the end of packet 3 is padded with the BOF code in the high word. Importantly, this means that the first word of the fourth packet will be the first word of the second frame even though the ultrasound frame size is not a multiple of the packet size.

TABLE 14

Example Packetization of Isochronous Head-to-Host Data

| Packet | Word | Lo Byte | Hi Byte |
|---|---|---|---|
| 1 | 1 | Data 1 Lo | BOF |
| (Frame 1) | 2 | Data 2 Lo | Data 2 Hi |
|  | 3 | Data 3 Lo | Data 3 Hi |
|  | 4 | Data 4 Lo | Data 4 Hi |
| 2 | 1 | Data 5 Lo | Data 5 Hi |
| (Frame 1) | 2 | Data 6 Lo | Data 6 Hi |
|  | 3 | Data 7 Lo | Data 7 Hi |
|  | 4 | Data 8 Lo | Data 8 Hi |
| 3 | 1 | Data 9 Lo | Data 9 Hi |
| (Frame 1) | 2 | Data 10 Lo | Data 10 Hi |
|  | 3 | Data 1 Lo | BOF |
|  | 4 | Data 1 Lo | BOF |
| 4 | 1 | Data 1 Lo | BOF |
| (Frame 2) | 2 | Data 2 Lo | Data 2 Hi |
|  | 3 | Data 3 Lo | Data 3 Hi |
|  | 4 | . . . | . . . |

The TSB 12LV31 (or 32) performs packetization of the isochronous data but system controller of packet boundaries via the ISORST signal. The system controller then uses this to reset its internal word-to-byte multiplexer as well as packetization circuitry. If it receives a frame marker from the FIFO then stops clocking data out of the FIFO until it receive a ISORST pulse.

The module interface defines how the various modules in the system are controlled by the VRAM controller. There are two types of modules, those that receive data from the four VRAMs which are shared (two on each analog board), and those that receive data from the VRAM on the digital board, (via the VRAM controller) which is dedicated. The two types of modules use different control signals to synchronize their operation.

Figure 5B:
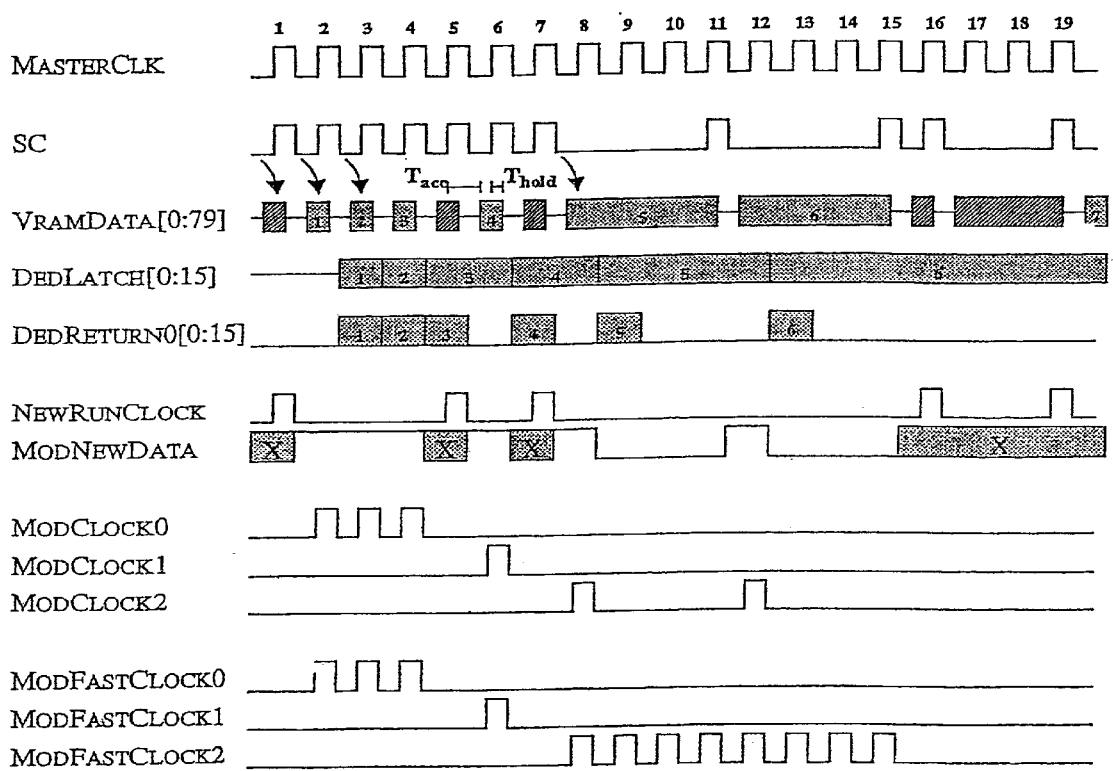
FIG. 5B schematically illustrates a timing diagram for the control of modules in the system.

Much of the timing depends on the speed of the runs of the module (shared/dedicated VRAM usage.) FIG. 5B shows typical timing for the different module interfacing modes for a typical program sequence.

As previously stated, VRAMDATA, the data from the loopback VRAM, control the execution. The diagonal shaded boxes denote header data used by the VRAM controller while the shaded boxes denote module data in FIG. 5B. The data in the four other VRAMs go to the modules. The data from the first VRAM is looped back into the system controller and then used for dedicated data supply for things like the TGC, feedback control, etc.

In clocks 1–4 in FIG. 5B a run of data at a rate 1/1 destined for module 0. The header is clocked out at clock 1. The pulse of NEWRUNCLOCK at clock 1 lets the modules know that the next clock will be the first in a run. They thus reset their internal run-related state if necessary. The data is clocked out during clocks 2, 3, and 4. Since the data is destined for module 0, the MODCLOCK0 is pulsed once per new data word. Module 0 should latch the data at VRAMDATA on the rising edge of MODCLOCK0.

Note that the access and hold times of the VRAM ($T_{acc}$ and $T_{hold}$ in FIG. 5B) must be observed carefully. Since the access time of the VRAM is 15 ns–25 ns depending on the speed grade the hold time can be as low as 4 ns, this does not leave a lot of margin when operating at data no earlier than $T_{clk}$–$T_{acc}$ before the rising edge of their module clock. (Any skew between SC and the MODCLOCK tightens this bound accordingly but due to the way the VRAM controller was designed to generate both signals as gated clocks from the same MASTERCLK the skew is minimal assuming that the loading conditions are not too dissimilar.) Given a master clock frequency of 33 MHz and the fast VRAM, this gives 15 ns slack. Using the slower VRAMs gives 5 ns slack.

The modules accepting data at the full rate must additionally make sure that they do not latch the data more than $T_{hold}$ after the rising clock. This is because the same clock is used to retrieve the next words from the VRAM. Thus in general modules should make sure to delay the data inputs at least as much as they delay the clock inputs to effectively clock at or before the rising edge of their module clock. This second constraint does not exist when 1/2, 1/4, or 1/8 rate data is used.

Since the first example is of 1/1 rate data, the MODULEFASTCLOCK0 signal follows the MODULECLOCK0 line. They will only differ when 1/2, 1/4, or 1/8 rate data is used.

Clocks 7–15 show a run of length 2 at rate 1/4 destined for Module 2. Thus new data will be clocked out of the VRAMs only once every $4^{th}$ master clock. Here MODULEFASTCLOCK2 will exhibit different behavior than MODULECLOCK2. Again the NEWRUNCLOCK at clock 7 signals that a new run is beginning on the next clock cycle. During clock 7, the VRAM controller has latched the header data indicating that the next run is for module 2 at a rate of 1/4. Also during clock 7, the VRAM generates the module data that the module will use. At clock 8, a MODCLOCK2 occurs, telling module 2 to latch in and use the VRAM's data. Note that the data will present until the master clock before the next MODCLOCK2.

Although MODCLOCK2 is only clocked once per new data word, MODULEFASTCLOCK2 is clocked once per master clock for the duration of the run. This is useful for modules, such as the beamformer which may only need data at a lower rate but need to perform computation at the full rate. The MODNEWDATA signal can also be used by modules using the MODFASTCLOCK lines to determine on which of the fast clocks new data has been presented.

Clocks 16–18 show the result of a pause command. Here the NEWRUNCLOCK is sequenced as usual but no MODCLOCK or MODFASTCLOCK is generated.

Figure 4B:
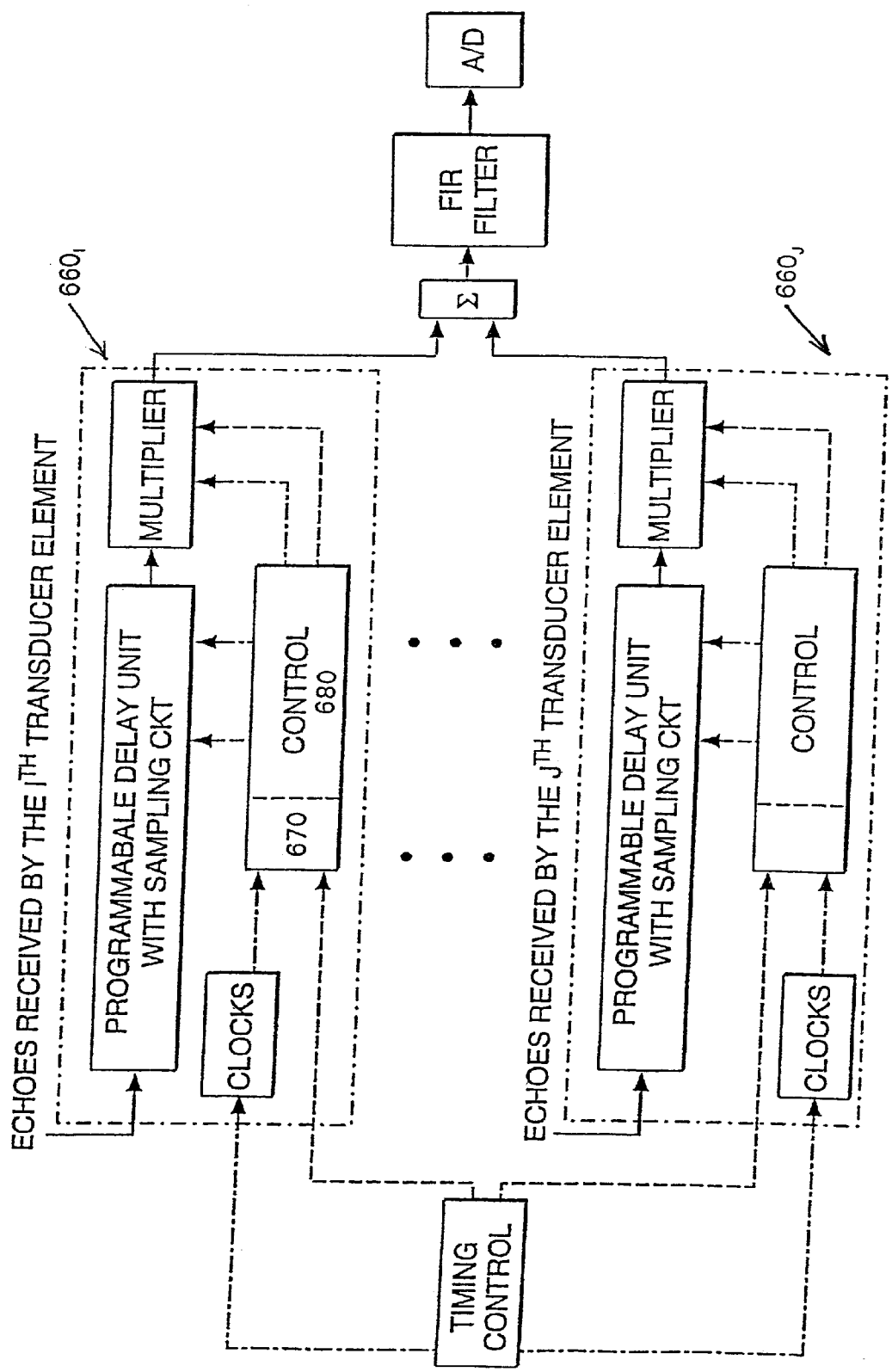
FIG. 4B illustrates another preferred embodiment of a beamformer in accordance with the invention.

As noted above, the particular embodiment was chosen based on a number of criteria, including simplicity of implementation using an FPGA. This motivated the use of VRAMs. An ASIC interface using more dense SDRAM requires at least some buffering, but this can be built into the controller, or alternatively, with the beamformer, T/R circuit or amplifier modules. In this way they receive bursts of data as opposed to the simple synchronous, continuous data that the above system supplies. The benefit is that SDRAMs are more dense and can provide data at higher rates, which reduces the parts count. Such a configuration is shown in FIG. 4B, for example, in which the 64 or 128 channel ($660_I$–$660_J$) system is configured on one or two printed circuit boards. In this two board system, the T/R circuit and the preamplifier/TGC circuit are fabricated in a single integrated circuit and are placed on one board with a CDP beamformer that is formed as a second integrated circuit. The beamformer control circuits can include the calculation of weighted inputs with processor 670. The memory for this system is an SDRAM located on the second board along with the system controller and the digital communication control circuit.

Returning to FIG. 3A, the standard Fire Wire cable 40 includes a plurality of Fire Wire signal lines 42 and a Fire Wire power line 44. In order to provide the necessary voltages, the Fire Wire power line 44 is fed to an inline DC-DC converter 300. The DC-DC converter 300 generates the necessary voltages and provides them over a plurality of power lines 46. These new power lines 46 are repackaged with the Fire Wire signal lines 42 in a custom cable 40'. In the probe housing 3', the Fire Wire signal lines 42 are connected to the Fire Wire chipset 220 and the custom power lines 46 are connected to a power distributor 48, which filters and distributes the various voltages over respective internal voltage lines 148A, 148B, 248. In addition, the power distributor 48 may perform additional DC-DC conversions, as described in more detail below.

The transmit/receive control chip is needed to interface with the transducer array. In a transmit mode, the chip can provide delays to the high-voltage driving pulses applied to each of the selected transducer elements such that the transmitted pulses will be coherently summed on the image place at the required transmit focus point. In a receive mode, it provides connection of the reflected sound waves received by a selected element to its corresponding amplifier. The functions of a multi-channel transmit/receive chip can be separated into two parts: a core function which provide low-voltage transmit/receive control and a buffer function which level shifts the low-voltage transmit/receive control into high voltage and directly interfaces with the transducer array. The core function of the transmit/receive chip includes a global counter which broadcasts a master clock and bit values to each channel processor; a global memory which controls transmit frequency, pulse number, pulse sequence and transmit/receive select; a local comparator which provides delay selection for each channel. For example, for a 60 MHZ clock and a 10 bit global counter, it can provide each channel with up to 17 us delay; a local frequency counter which provides programmable transmit frequency; a local pulse counter which provides different pulse sequences. For example, a 6-bit counter can provide programmable transmitted pulse lengths from one pulse up to 64 pulses; a locally programmable phase selector which provides sub-clock delay resolution. For example, for a 60 MHz master clock and a two-to-one phase selector provides 8 ns delay resolution.

While typically the period of the transmit-chip clock determines the delay resolution, a technique called programmable subclock delay resolution allows the delay resolution to be more precise than the clock period. With programmable subclock delay resolution, the output of the frequency counter is gated with a phase of the clock that is programmable on a per-channel basis. In the simplest form, a two-phase clock is used and the output of the frequency counter is either gated with the asserted or Deasserted clock. Alternatively, multiple skewed clocks can be used. One per channel can be selected and used to gate the coarse timing signal from the frequency counter.

Figures 3B, 3C:
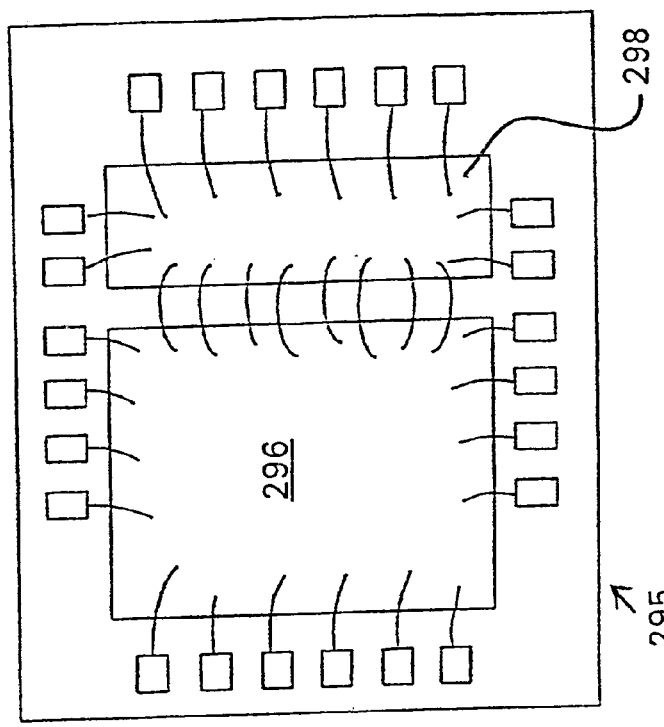
FIGS. 3B and 3C illustrate embodiments of the transmit/receive circuit.

As can be seen in FIG. 3B, a semiconductor process that can support both high-voltage and low-voltage operations is ideally matched for a single-chip solution to the transmit/receive chip described above. The core function of the transmit/receive chip can be implemented on low-voltage transistors to reduce power consumption. The level-shifting function can be implemented on high-voltage transistors to provide the necessary driving pulses to the transducer array. However, only selected semiconductor processes can make the integration of both high-voltage (buffer 292) and low-voltage transistors (294) on one chip 290 possible. As a result, the high/low voltage process has been so far offered only with 0.8-to-1 um-design rules. With these design rules, a 64-channel transmit/receive chip can easily be integrated on a single chip in less than 1 cm$^2$ chip area.

In order to save power and silicon area, a multi-chip module 295 can be used to implement a transmit/receive chip. For example, a deep-sub-micron process can be used to implement the core function 296 of the module, and a separate process can be used to implement the buffer 298 function. As shown in FIG. 3C, the multi-chip set can be mounted in a single package to realize the transmit/receive control function. With multi-chip module approach, a 128-channel transmit/receive controller can easily be integrated on one package.

Figure 3D:
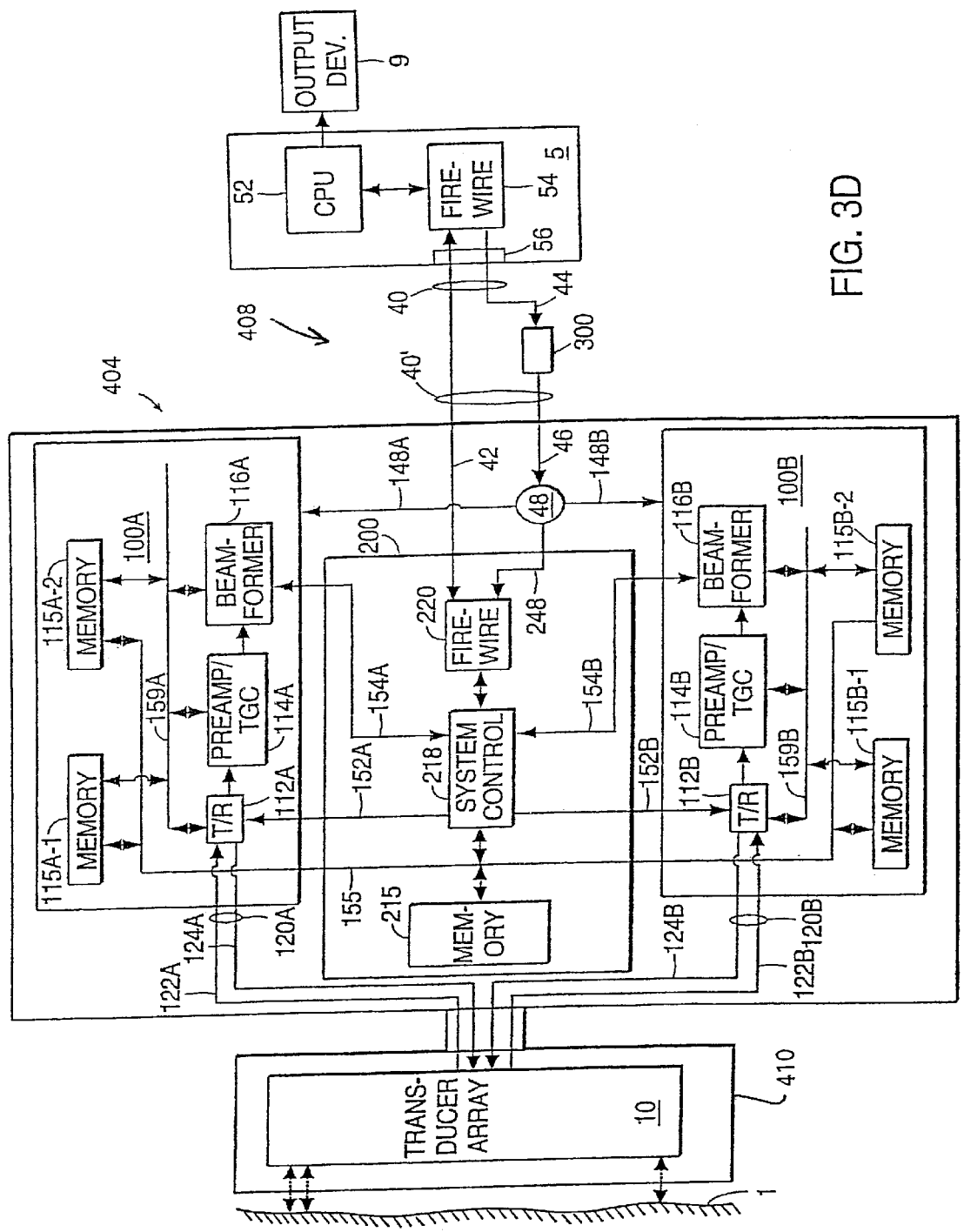
FIG. 3D illustrates an alternate embodiment in which the probe housing is separated from the interface housing by a cable.

FIG. 3D illustrates an alternate embodiment in which the transducer array 10' is located in a separate probe housing 410 connected to the interface housing 404 by a cable 412. Such a system is also illustrated in connection with FIG. 12. Note that another embodiment involves a probe housing in which certain circuit elements such as the transmit/receive circuitry and/or the preamp/TGC circuitry is included with the transducer array while the beamformer, system control and memory circuits remain in the interface. The system in FIG. 3D provides for the use of standard probes and a beamformer interface that weighs less than 10 lbs and which can be connected to a standard personal computer. The interface 404 has a volume of less than 1500 cm$^3$ and a weight that is preferably less than 5 lbs.

Figure 6A:
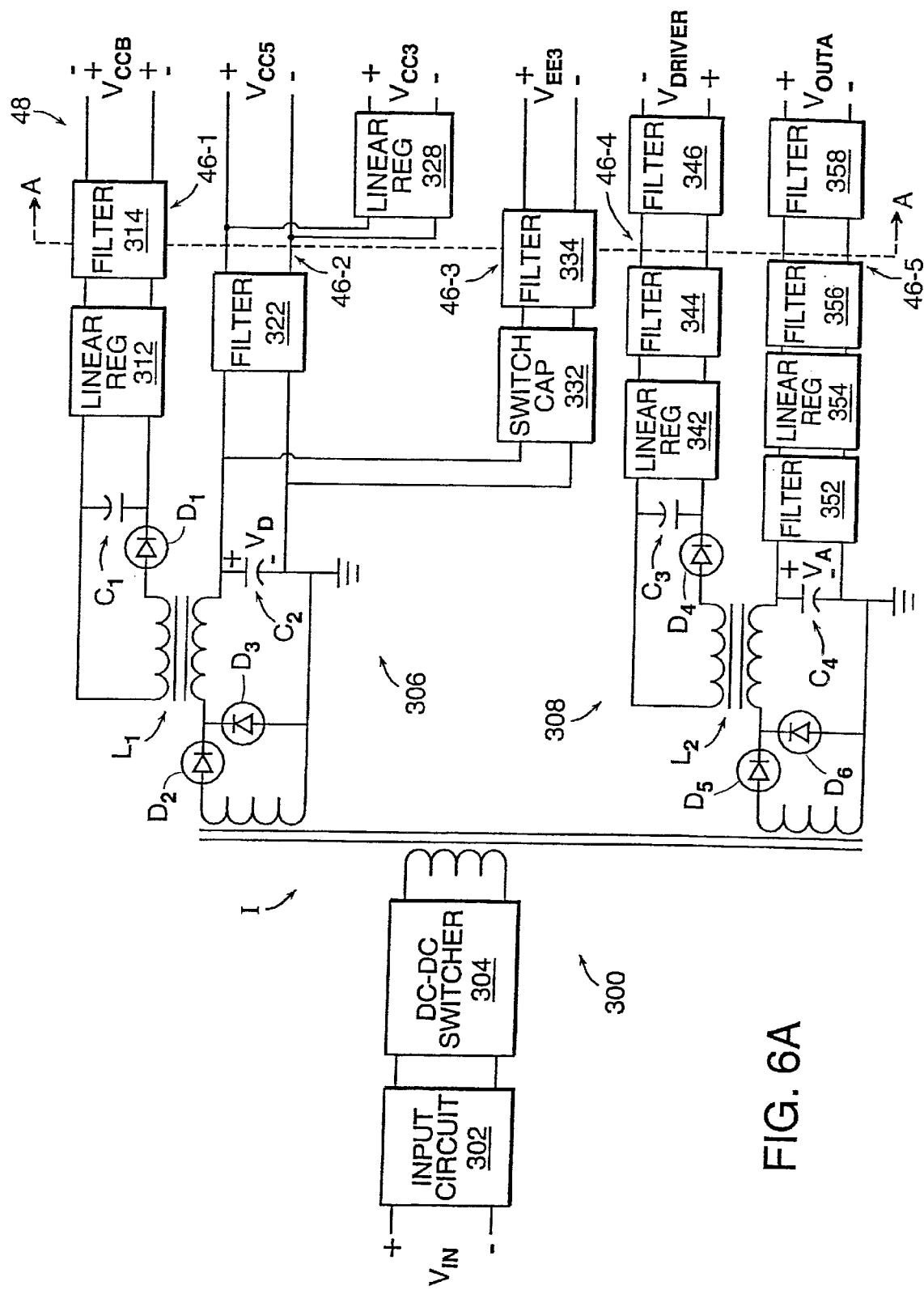
FIGS. 6A–6C are diagram of exemplary FireWire-based DC-DC converters.
Figure 6B:
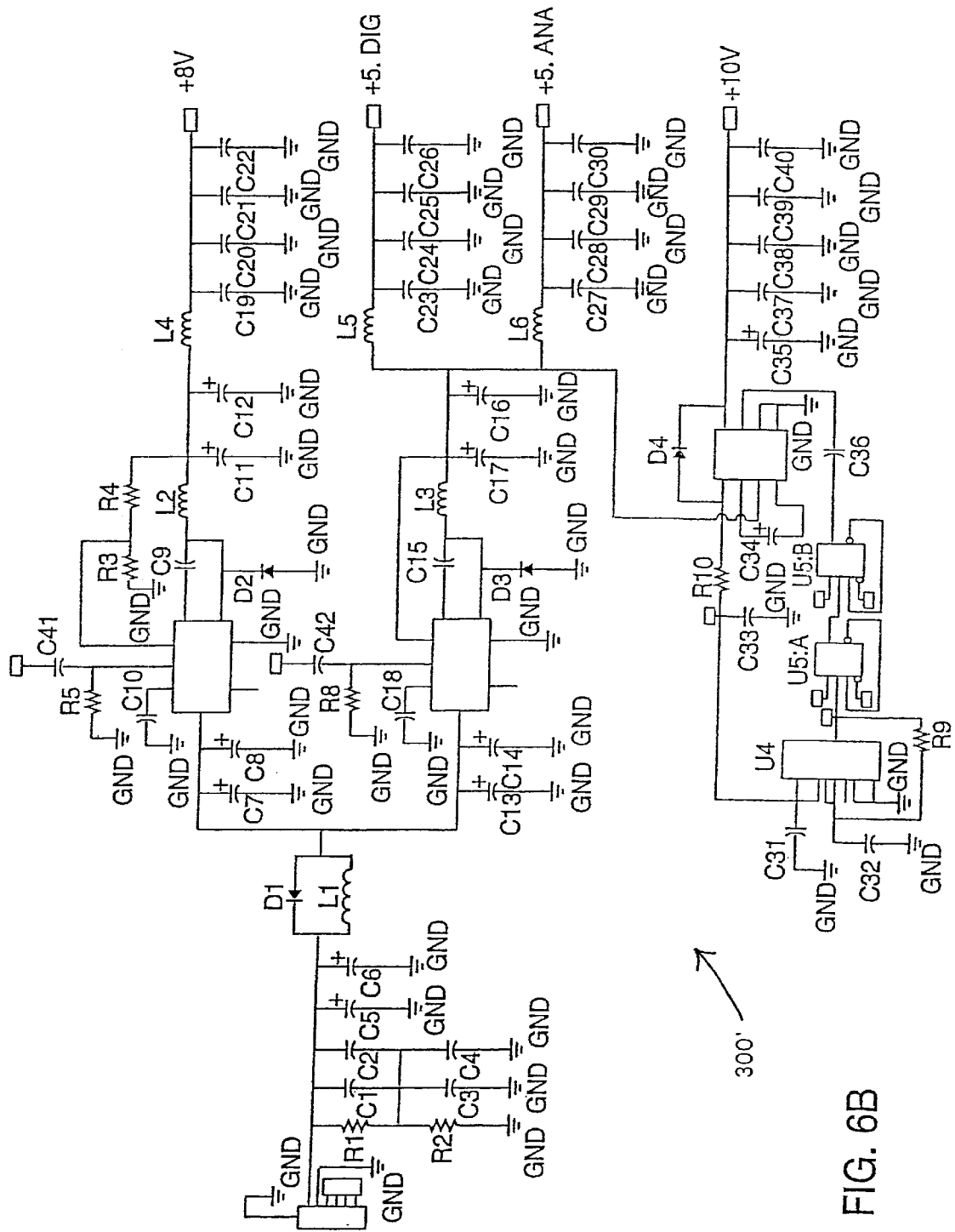
Figure 6C:
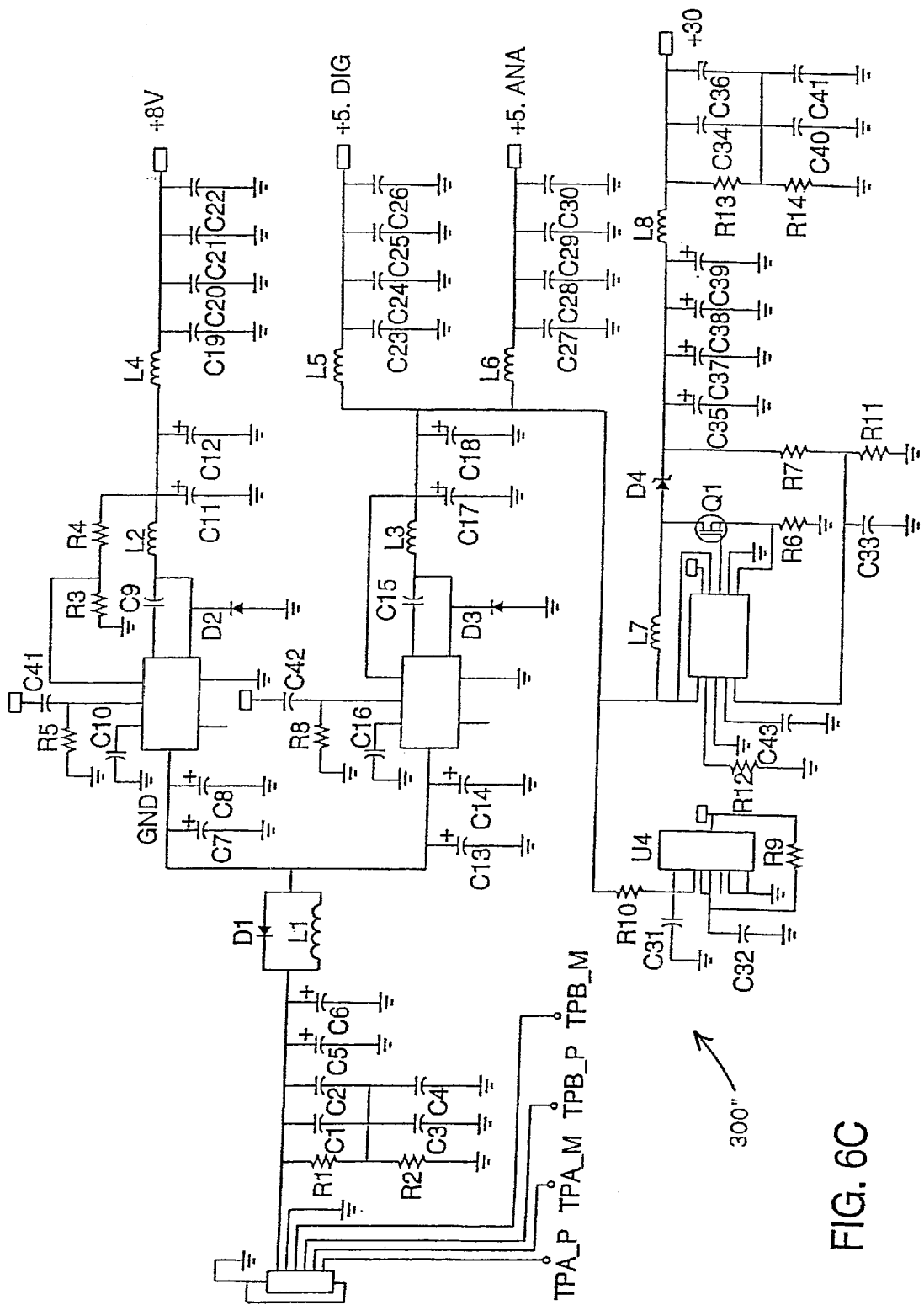

FIGS. 6A–6C are diagrams of exemplary FireWire-based DC-DC converters. The role of the converter is to accept the Fire Wire (IEEE 1394) voltage input and to output DC voltages for use by the probe electronics. In particular, the converter receives an 8–40 V DC input (Vin) (per IEEE 1394 specification) and converts that voltage to the required voltages. The details of the converter 300 will therefore vary based on the specific voltage requirements of the probe electronics.

Referring to FIG. 6A, the converter 300 generates output voltages of +5 V DC, −3 V DC, +7 V DC, +5 V DC, and +10 V DC. In input circuit 302 comprising a fuse and filter receives the Fire Wire voltage input. After filtering, the input voltage is provided to a DC-DC switcher 304 which generates a square wave pattern from a constant voltage. In particular, the DC square wave is fed to a transformer T. Separate taps off from the transformer T provide a 5 V digital DC voltage (Vd) to a digital voltage transformation circuit 306 and a 5 V analog DC voltages (Va) to an analog voltage transformation circuit 308. Based on the duty cycle of the waveform, the waveform is rectified and filtered in the transformation circuits 306, 308 to generate lower DC voltages.

For digital voltages, the 5 V DC waveform is rectified using diodes D2 and D3 and smoothed by capacitor C2. A filter 322 directly coupled to the digital DC voltage (Vd) to provide the +5 V DC voltage (Vcc5) is provided over a respective power line 46-2 to power the digital electronics. In the power distributor 48, a linear regulator 328 taps the 5V DC voltage (Vcc5) to provide a regulated 3 V DC voltage (Vcc3). A switch capacitor 332 tapped off from the digital DC voltage (Vd) and a filter 334 are used to produce the −3 V DC voltage (Vee3) for the integrated circuit substrate bias voltage to the charge coupled devices (CCD). That voltage is provided over a respective power line 46-3. An inductive coupling L1 transforms the 5 V DC voltage to 7 V DC, which is rectified by a diode D1 and smoothed by a capacitor C1. A linear regulator 312 and a filter 314 provides a regulated 7 V DC voltage (Vccb) for the charge coupled devices. That voltage is provided over a respective power line 46-1. As illustrated, filters 314 and 334 have components which are split between the DC-DC converter 300 and the power distributor 48.

For analog voltages, the 5 V waveform is rectified using diodes D5 and D6 and smoothed by capacitor C4. A first filter 352 directly coupled to the analog DC voltage (Va), a linear regulator 354 and a second filter 356 provide a 5 V DC voltage (Vouta) over a respective power line 46-5 for the analog pre-amplifiers. In the power distributor 48 a filter 358 reduces ripple generated while the voltage was transmitted through the cable. An inductive coupling L2 transforms the analog DC voltage (Va) into 10 V DC for use by the high-voltage transducer drivers. This voltage is rectified by a diode D4 and smoothed by a capacitor C3. A linear regulator 342 and a filter 344 yield the driver voltage (Vdriver) transmitted over a respective power line 46-4. The power distributor 48 also includes a filter 346 to reduce ripple generated while that voltage was transmitted through the cable.

The filters comprise conductors and capacitors which are designed to provide a low pass filter frequency response. The purpose of the low pass filters is to reduce the amplitude of high frequency ripple on the DC voltage created by the DC-DC switching circuitry.

The linear DC voltage regulators are implemented by operational amplifier with a pass-transistor in the feedback path. Typically, these devices are relatively efficient because they dissipate power through a resistor to produce a new output voltage.

The switch capacitor charges a relatively large capacitor to a specified voltage. Using analog switches, it then reverses the plates of the capacitor to produce the negative voltage. This configuration is often referred to as a charge pump converter.

FIG. 6B is a schematic diagram of an alternative DC-DC converter. The converter 300' generates a +8 V DC, +5 V DC (digital), +5 V DC (analog), and +10V DC.

FIG. 6C is a schematic diagram of an alternative high voltage DC-DC converter. The converter 300" is similar to the converter 300' of FIG. 6B, except that the +10 V DC output is replaced by a high voltage +30 V DC supply. Converters can supply voltages up to 200 V.

Figure 7B:
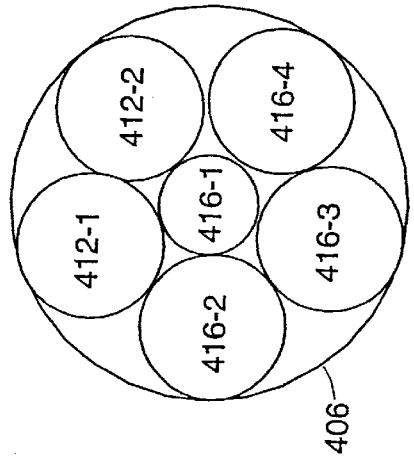
FIGS. 7A–7B are schematic diagrams of a custom cable for use with the DC-DC converter of FIG. 6B or 6C.
Figure 7A:
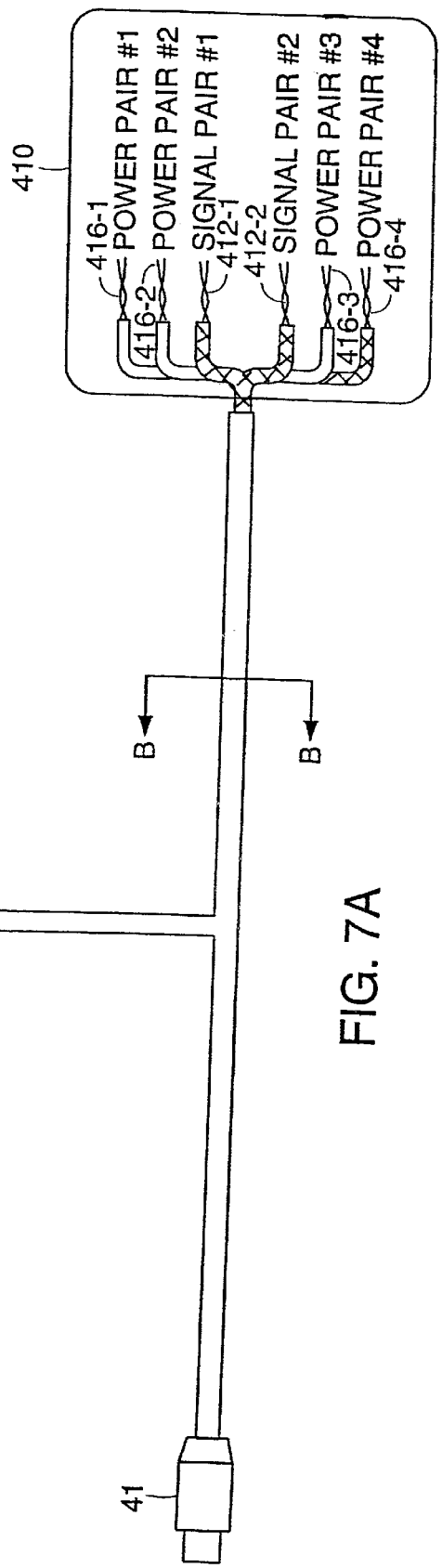

FIGS. 7A–7B are schematic diagrams of a custom cable for the DC-DC converter of FIG. 6B or 6C. As previously described, the custom cable 40' is a cable medium connection between the power case 300 and the probe 3'. The custom cable 40' includes three shielded twisted pair and three unshielded twisted pair connectors. Two shielded twisted pairs 412-1, 412-2 are used as the serial bus and carry pull voltage differential data signals as defined by the Fire Wire protocol. The other twisted pair connectors provide different power signals 416-1, 416-2, 416-3, with the analog power provided by a shielded twisted pair 416-4. The cable environment uses the two low voltage differential signals to connect devices and a non-cyclic topology had approximately 400 Mbps data rates. The cable arbitration system uses a self configuring hierarchical request/grant protocol that supports hot plugging and widely varying physical topologies.

FIG. 7A is a schematic diagram of a complete cable assembly. The cable 40', as shown, includes the two signal lines 412-1, 412-2 with respective shielding. It is advantageous for the signal pairs to be closely matched for skew and other factors. The analog power twisted pairs 416-4 are also shielded. The remaining power twisted pair wires are insulated with respective insulation. The exterior of the cable 40' is an insulating outerjacket 406.

FIG. 7B is a cross-sectional schematic diagram of the cable assembly taken along line B—B of FIG. 8A.

Figure 8:
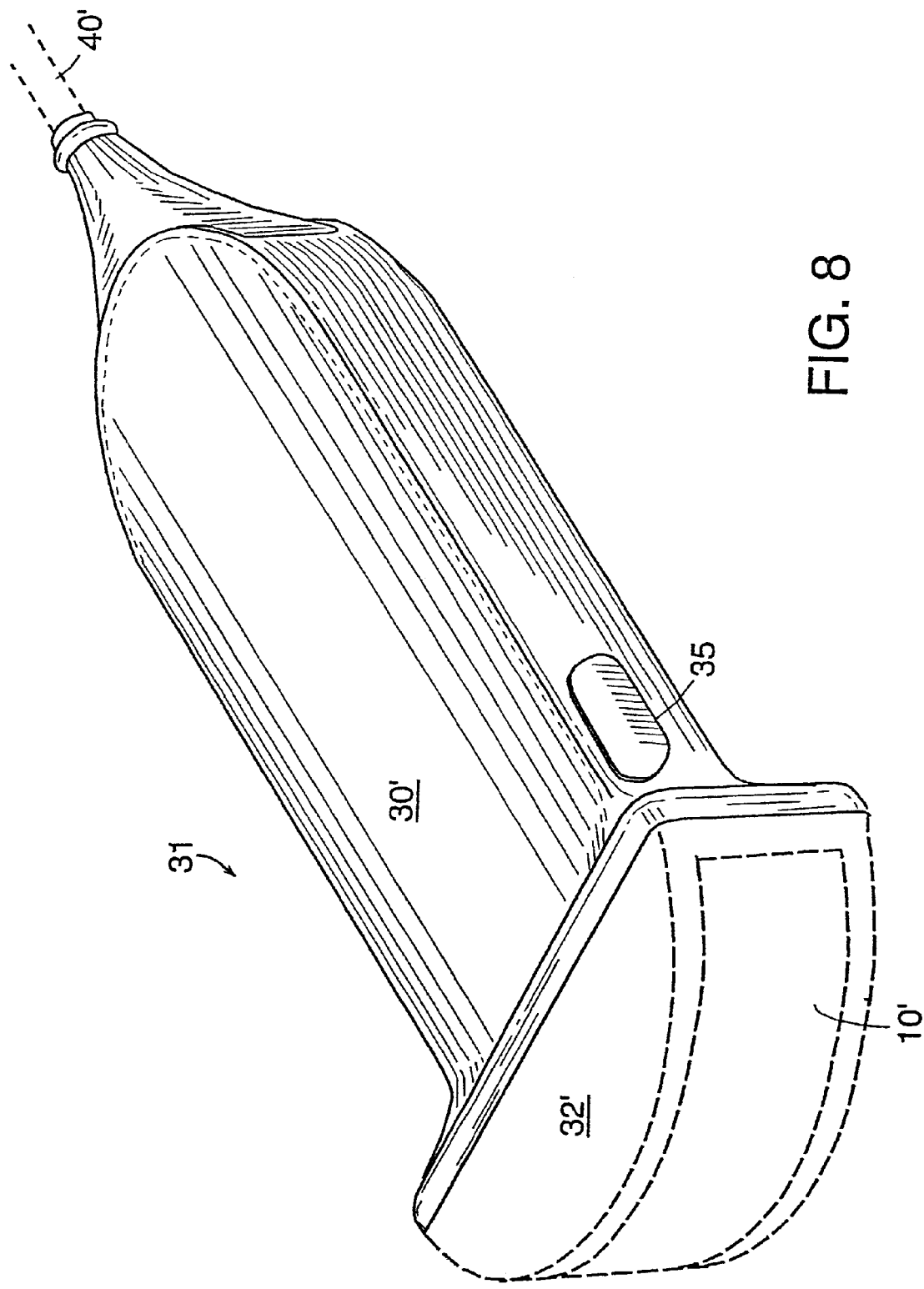
FIG. 8 is a perspective view of an ultrasound probe.

FIG. 8 is a perspective view of an ultrasound probe. The probe 3' includes a probe housing 30' and a curved scan head 32' having a transducer array 10'. A button 35 can optionally be provided for use by an operator to turn probe power on or off.

Figure 9:
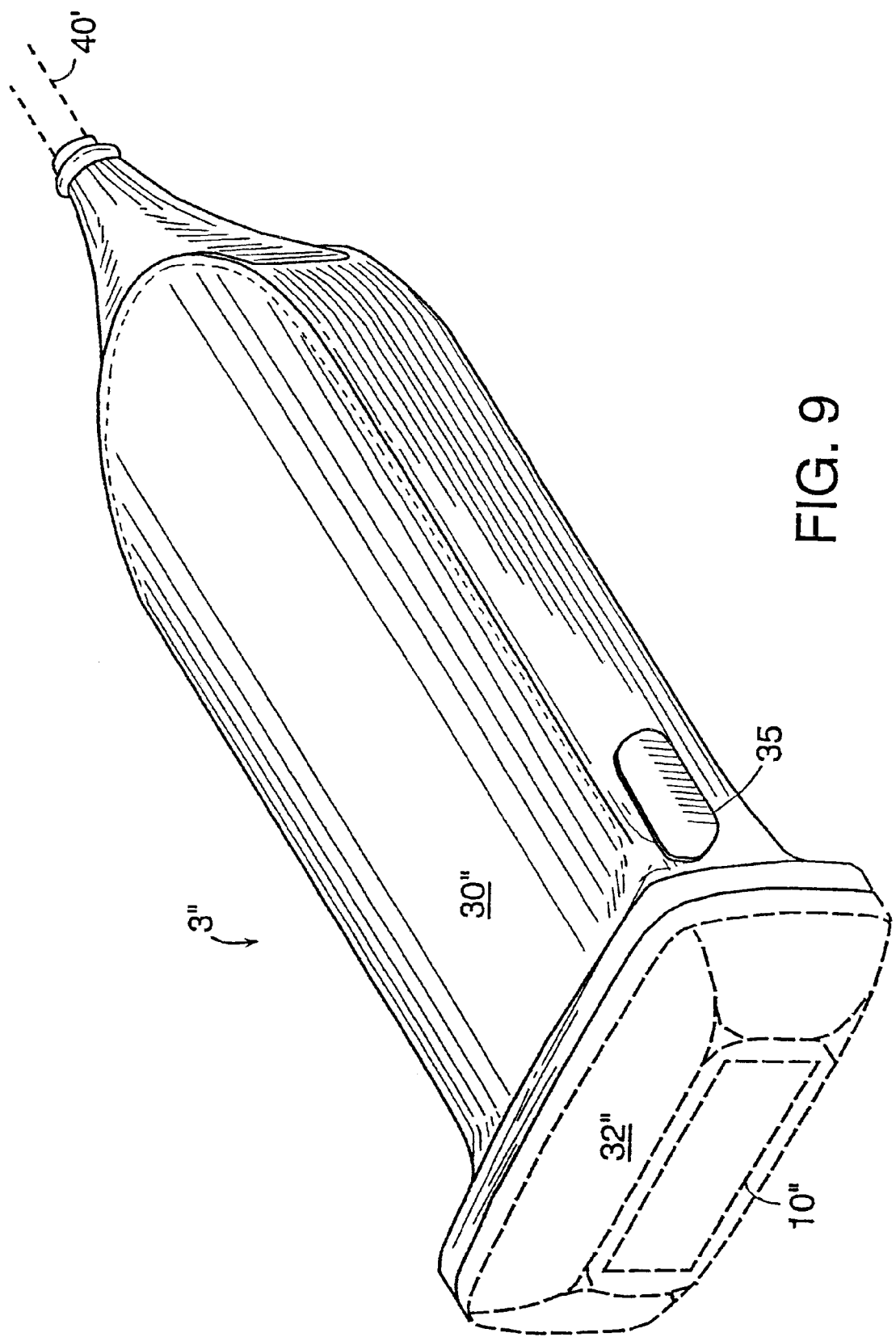
FIG. 9 is a perspective view of another ultrasound probe.

FIG. 9 is a perspective view of another ultrasound probe. The probe 3" includes a probe housing 30" and data linear scan head 32" having a transducer array 10". Again, an optional button 35 is for use by an operator to turn probe power on or off.

It should be understood that the exact position of the button 35 will be based on ergonomics. Although the button 35 could be placed on the top or bottom surface of the probe housing, the side location is preferred by most operators. In addition, because the probes can be used in a hospital operating room, the button area should be easy to clean and resistive to hospital cleaning agents.

Figure 10:
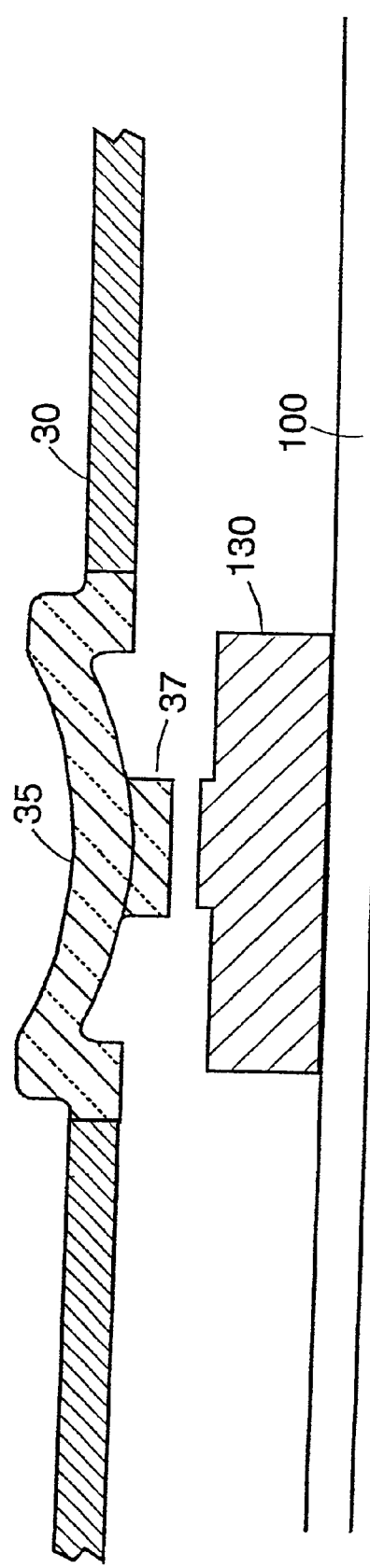
FIG. 10 is a schematic diagram of a button mechanism for the ultrasonic probes.

FIG. 10 is a schematic diagram of a button mechanism for use with the ultrasonic probes. The button 35 is bonded to the housing 30 to create a smooth interface. The button 35 can be a flexible membrane having a rigid contact surface 37 on its interior surface. An electromechanical switch 130 mounted to an analog circuit board 100 is activated when the button 35 is depressed.

Figure 11:
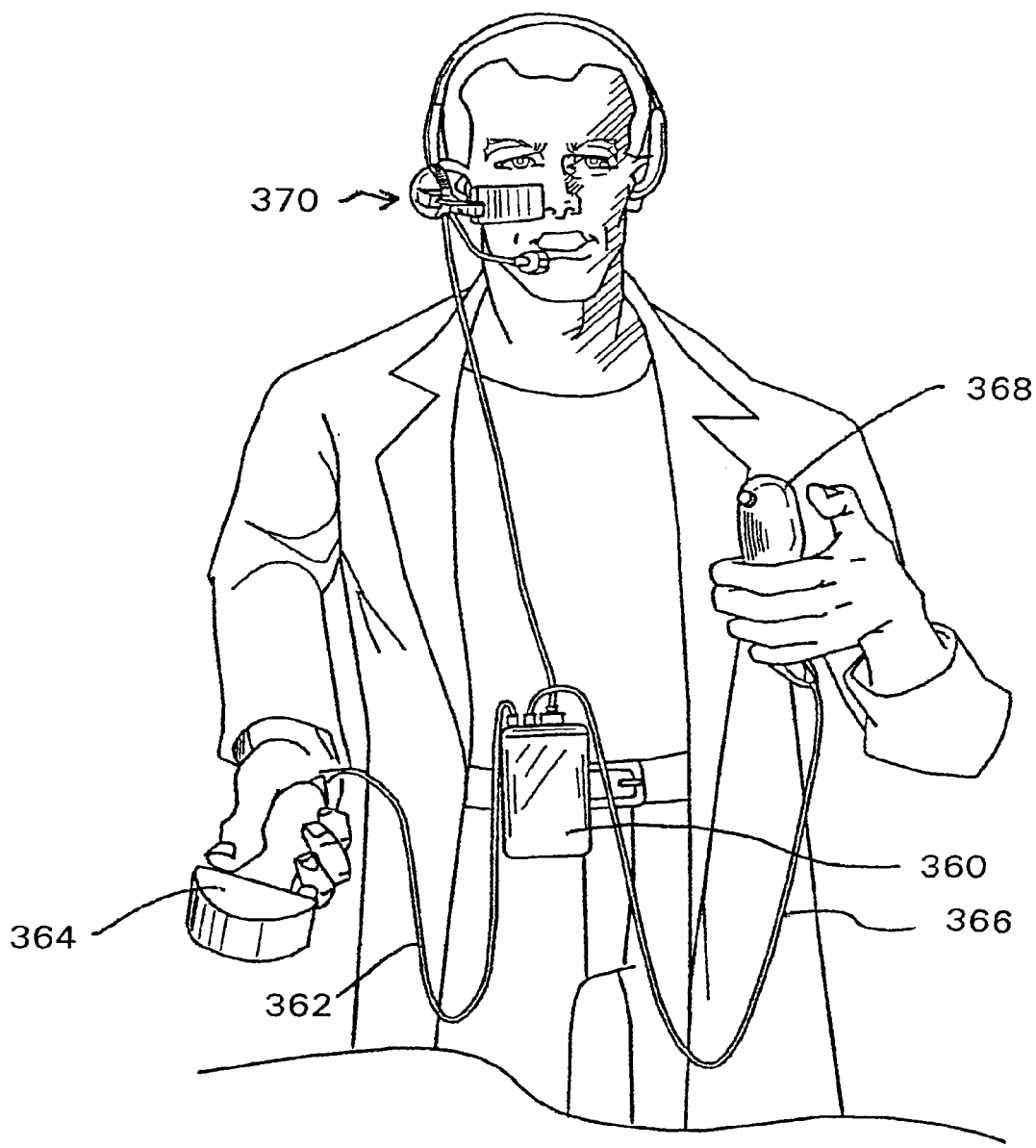
FIG. 11 illustrates a wearable or body mounted ultrasound system in accordance with the invention.

FIG. 11 illustrates a wearable ultrasound imaging system that can include a belt mounted computer 360 or interface connected big cable 362 to handheld probe 364, a second handheld unit 366 that can include various controls including a mouse control and buttons to freeze the image displayed or to store a particular image in electronic memory. The unit 366 can be connected by wireless (RF or infrared) connection or by cable 366 to housing 360. The computer 360 can be connected to a desktop, laptop or handheld display or can be connected by cable to a headmounted display system 370 that includes a microphone, a pair of speakers for audio and a high resolution display positioned adjacent the user's eye.

Figure 12:
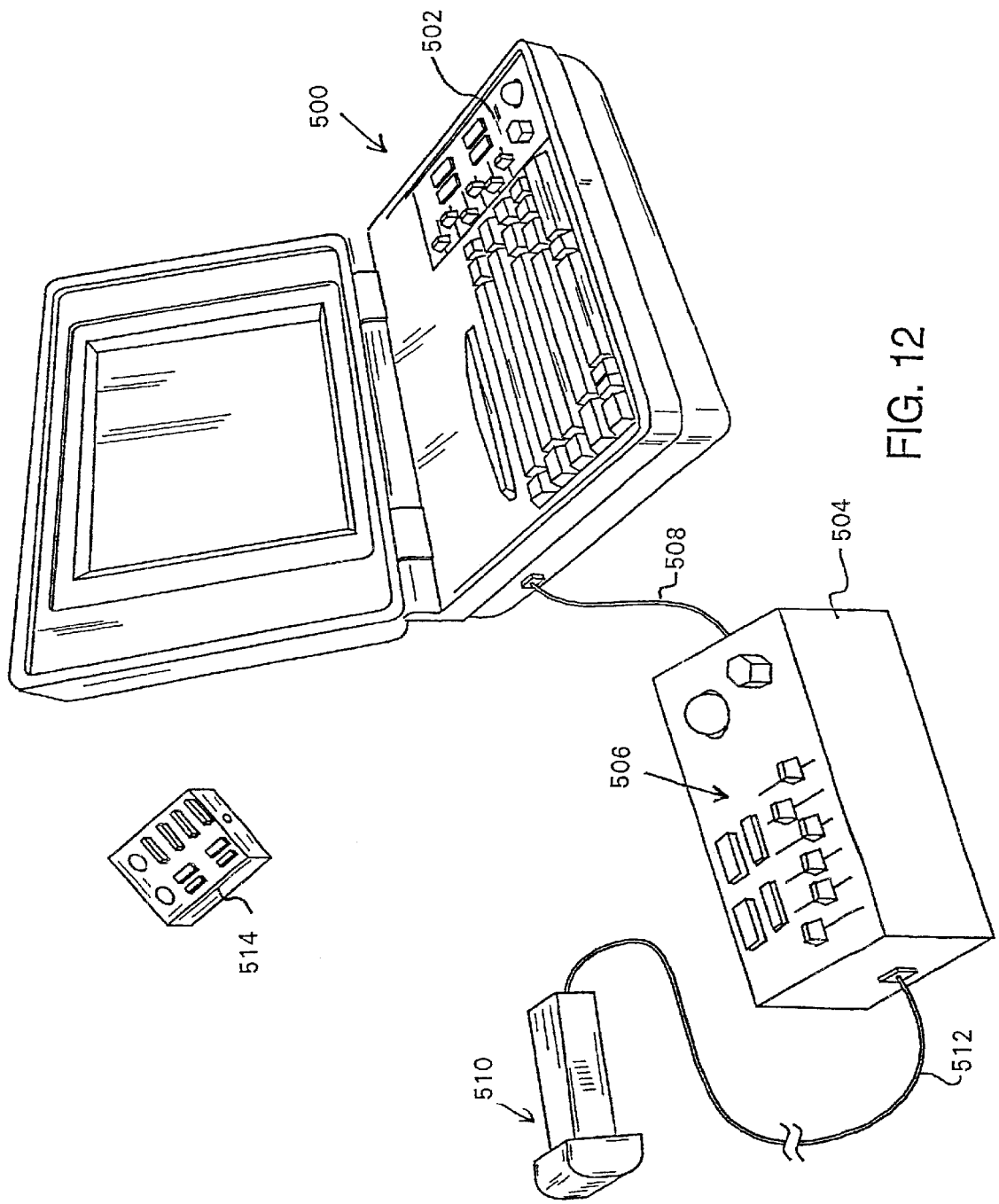
FIG. 12 illustrates an interface system using a standard communication link to a personal computer.

Another preferred embodiment is illustrated in FIG. 12 in which a laptop computer 500, having a flat panel display and a standard keyboard, has been programmed to perform scan conversion, doppler processing etc. on a beamformed representation of the region of interest that has been transmitted from interface housing 504 along a standard communications link such as cable 508 that conforms to the IEEE 1394 Fire Wire standard or the USB 2.0 standard for example. The computer 500 and/or the interface can optionally include a control panel 502, 506, that can be used to control the study being conducted. Alternately, an additional remote controller 514 can be used to control system operation. The interface 504 can house the circuit boards on which the beamformer, memory, system controller and digital communication circuits are mounted. The interface 504 is connected to the handheld probe 510 with a cable that is preferably between two feet and six feet in length. The transmit/receive and/or the preamplifier/TGC circuits can be in the probe housing 510 or in the interface housing 504. The computer can also be configured for gigabit ethernet operation and for transmitting video and image data over networks to remote systems at clinics or hospitals. The video data can also be sent to a VCR or standard video recorder or video camera with an IEEE 1394 part for recording on videotape. The VCR or video camera can be controlled using the computer.

Returning to FIG. 1, the host 5 can be a desktop, laptop palmtop or other portable computer executing software instructions to display ultrasound images. In addition to real-time B-mode ultrasound images for displaying soft-tissue structures in the human body, Doppler ultrasound data can be used to display an estimate of blood velocity in the body in real time. Three different velocity estimation systems exist: color-flow imaging (CFI), power-Doppler and spectral sonogram.

The color-flow imaging modality interrogates a specific region of the body, and displays a real-time image of mean velocity distribution. The CFI's are usually shown on top of the dynamic B-mode image. To determine the direction of blood flow, different colors indicate velocity toward and away from the transducer.

While color flow images display the mean or standard deviation of the velocity of reflectors (i.e., blood cells) in a given region, power Doppler (PD) displays a measurement of the amount of moving reflectors in the area, similar to a B-mode image's display of the total amount of reflectivity. A PD image is an energy image in which the energy of the flow signal is displayed. These images give no velocity information but only show the location of flow.

The spectral Doppler or spectral sonogram modality utilizes a pulsed-wave system to interrogate a single range gate and displays the velocity distribution as a function of time. This sonogram can be combined with a B-mode image to yield a duplex image. Typically, the top side of the display shows a B-mode image of the region under investigation, and the bottom shows the sonogram. Similarly, the sonogram can also be combined with the CFI image to yield a triplex image. Thus, the time for data acquisition is divided between acquiring all three sets of data. Consequently, the frame rate of the complex image is generally decreased, compared to either CFI or duplex imaging.

A pulsed-Doppler processor for color-flow map applications is now described. Color Doppler (CD) or color-flow imaging combines, in a single modality, the capabilities of ultrasound to image tissue and to investigate blood flow. CD images consist of Doppler information that can be color-encoded and superimposed on a B-mode gray-scale image.

Color-flow imaging is a mean velocity estimator. There are two different techniques in computing the mean velocity. First, in a pulsed Doppler system fast fourier transformer (FFTs) can be used to yield the velocity distribution of the region of interest, and both the mean and variance of the velocity profile can be calculated and displayed as a color flow image. The other approach uses a one-dimensional auto correlation.

An estimate of the mean velocity in the range gate gives an indication of the volume flow rate. Given that the frequency of the reflected, range-gated signal is proportional to the flow velocity, the spatial mean velocity is determined by the mean angular frequency.

$$\bar{\omega} = \frac{\int_{-\infty}^{+\infty} \omega P(\omega) d\omega}{\int_{-\infty}^{+\infty} P(\omega) d\omega} \quad (1)$$

Here, $P(\omega)$ is the power-spectral density of the received, demodulated signal. The inverse Fourier transform of the power-spectral density is the autocorrelation:

$$R(\tau) = \int_{-\infty}^{+\infty} P(\omega) \exp(j\omega\tau) d\omega. \quad (2)$$

The derivative of the autocorrelation with respect to $\tau$ is:

$$\dot{R}(\tau) = \int_{-\infty}^{+\infty} P(\omega) \exp(j\omega\tau) d\omega \quad (3)$$

Substituting Eqs. (2) and (3) into Eq. (1) yields:

$$\bar{\omega} = \frac{\dot{R}(0)}{jR(0)}. \quad (4)$$

Therefore, the mean velocity estimator can be reduced to an estimation of the autocorrelation and the derivative of the autocorrelation. The estimator given by the proceeding expression can be calculated when data from two returned lines are used, i.e., $$\bar{\omega} = -f_{prf} \arctan(\Phi), \quad (5)$$

where $$\Phi = \frac{\frac{1}{N_c - 1} \sum_{i=0}^{N_c-2} y(i+1)x(i) - x(i+1)y(i)}{\frac{1}{N_c - 1} \sum_{i=0}^{N_c-2} y(i+1)x(i) - y(i+1)y(i)} \quad (6)$$

$f_{prf}$ is the pulse repetition frequency, and $N_c$ are the number of lines used in autocorrelation estimator. In practice, more then 2 lines are used to improve the signal-to-noise ratio. Data from several RF lines are needed in order to get useful velocity estimates by the auto-correlation technique. Typically, between 8 and 16 lines are acquired for the same image direction. The lines are divided into range gates throughout the image depths and the velocity is estimated along the lines.

For duplex imaging, the CFI pulses are interspersed between the B-mode image pulses. For CFI pulses, it is known that a longer duration pulse train gives an estimator with a lower variance, however, good spatial resolution necessitates a short pulse train. Consequently, a separate pulse train must be used for the B-mode image, because the CFI pulse train is too long for high-resolution, gray-scale images.

For color-flow imaging, CFI, the velocity estimator is given by Eq. (5). This can be computed by serial processing, since the arrival of samples for a new line results in the addition of the new data to an already calculated sum. Four multiplications, three additions, and a subtraction are performed for each range gate and each new line. Stationary echo cancellation is also performed for each new sample. A filter with $N_e$ coefficients necessitates $2N_e$ multiplications and additions per gate and line.

Assuming that all data samples are used for CFI imaging, the total number of multiplications and additions per second is $$N_{ops} = (2N_e + 2)Mf_0, \quad (7)$$

where $Mf_0$ is the number of data samples per second. This is a conservative value since B-mode lines are interspersed with CF imaging lines causing time to be lost switching between modes. It follows that $$N_{ops} = \eta(nN_e + 2)Mf_0 \frac{N_c - N_b}{N_c}, \quad (8)$$

where $N_c$ is the number of CFI lines per estimate, $N_B$ is the number of B-mode image lines interspersed between CFI lines, and $\eta$ denotes the effective time spent on acquiring useful data.

For a CFI system using 8 lines per estimate, an echo cancellation filter with 4 coefficients and an 8 times-oversampled 4 MHZ pulse, one B-mode line is interspersed between CFI lines and 80% of the time is consumed acquiring data. Using Eq. (7), the number of calculations per second is $N_{ops}=172\times10^6$. This is within the capability of a current Pentium-class laptop computer. Thus, all of the CFI signal processing can be performed in software using a state-of-the-art microprocessor.

While Color Flow Imaging (CFI) has been an effective diagnostic tool in clinical cardiovascular applications, Power Doppler (PD) imaging provides an alternative method of displaying the blood stream in the insonified regions of interest. While CF imaging displays the mean or standard deviation of the velocity of reflectors (e.g., blood cells) in a given region, PD displays a measurement of the density of moving reflectors in the area, similar to the B-mode image's display of reflectivity. Thus, Power Doppler is akin to a B-mode image with stationary reflectivity suppressed. This is particularly useful for viewing moving particles with small cross-sectional scattering, such as red blood cells.

Power Doppler displays the integrated Doppler power instead of the mean frequency shift as used for color Doppler imaging. As discussed in the previous section, the color-flow mapping is a mean-frequency estimator that is expressed as $$\bar{\omega} = \frac{\int_{-\infty}^{+\infty} \omega P(\omega) d\omega}{\int_{-\infty}^{+\infty} P(\omega) d\omega} \quad (9)$$

where $\bar{\omega}$ represents mean-frequency shift and $P(\omega)$ is the power-spectral density of the received signal. The inverse Fourier transform of the power-spectral density is the auto-correlation:

$$R(\tau) = \int_{-\infty}^{+\infty} P(\omega) \exp(j\omega\tau) d\omega. \quad (10)$$

The total Doppler power can be expressed as the integral of the power-spectral density over all angular frequencies, $$pw = \int_{-\infty}^{+\infty} P(\omega) d\omega. \quad (11)$$

By observing the similarities between Eq. (2) into (10), it follows that the 0th lag of the auto-correlation function can be used to compute the integrated total Doppler power.

$$R(0) = \int P(\omega) \exp(j\omega 0) d\omega = \int P(\bar{\omega}) d\omega = pw. \quad (12)$$

In other words, the integrated power in the frequency domain is the same as the integrated power in the time domain and hence the power Doppler can be computed from either the time-domain or the frequency-domain data. In either case, the undesired signals from the surrounding tissue, such as the vessel walls, should be removed via filtering. This calculation is also referred to as a Wall filter.

In a preferred embodiment, the PD can be computed in software running on a microprocessor; similar to the computation of the CFI processing described above. Parallel computation units, such as those in the Intel Pentium TM and Pentium II's MMX coprocessors, allow rapid computation of the required functions. A Digital Signal Processor (DSP) can also be used to perform this task. For either case, a software implementation permits the flexibility to change and investigate digital signal processing algorithms and transmitting signals that achieve the best performance as region of interest changes.

The above showed that the frequency content of the Doppler signal is related to he velocity distribution of the blood. It is common to devise a system for estimating blood movement at a fixed depth in tissue. A transmitter emits an ultrasound pulse that propagates into and interacts with tissue and blood. The backscattered signal is received y the same transducer and amplified. For a multiple-pulse system, one sample is acquired for each line or pulse emitted. A display of the distribution of velocities can be made by Fourier transforming the received signal and showing the result. This display is also called a sonogram. Often a B-mode image is presented along with the sonogram in a duplex system, and the area of investigation, or range gate, is shown as an overlay on the B-mode image. The placement and size of the range gate is determined by the user. In turn, this selects the epoch for data processing. The range gate length determines the area of investigation and sets the length of the emitted pulse.

The calculates spectral density is displayed on a screen with frequency on the y-axis and time on the x-axis. The intensity of a pixel on the screen indicates the magnitude of the spectrum; thus, it is proportional to the number of blood scatterers moving at a particular velocity.

The range gate length and position are selected by the user. Through this selection, both emitted pulse and pulse repetition frequency are determined. The size of the range gate is determined by the length of the pulse. The pulse duration is $$T_p = \frac{2l_g}{c} = \frac{M}{f} \quad (13)$$

where the gate length is $l_g$ and M is the number of periods. The gate duration determines how rapidly pulse echo lines can be acquired. This is referred to as the pulse-repetition frequency or $$f_{prf} \leq \frac{c}{2d_0}, \quad (14)$$

where $d_0$ is the distance to the gate. For example, a 4 period, 7 MHZ pulse is used for probing a blood vessel lying at a depth of 3 cm with a 10 ms observation time.

The gate length is computed as $$l_g = 0.44 \text{ mm}. \quad (15)$$

The pulse-repetition frequency is $$f_{prf} \leq \frac{c}{2d_0} \approx 25 \text{ KHz}. \quad (16)$$

The total number of independent spectral lines is $N=T_{obs}f_{prf}=250$. It follows that the maximum detectable velocity is $$v_{max} = \frac{f_{prf}}{2} \frac{c}{2f_0} = 1.4 \text{ m/s}. \quad (17)$$

Using a 256-point FFT to compute the Fourier transform, the total number of multiplications/additions per second required for the preceding example is less than 10 MOPs/s. In a preferred embodiment, the sonograph computation can be carried out in software running on a microprocessor (similar to the computation of the CFI processing described above). Parallel computation units, such as those inside the Intel Pentium TM and Pentium II's MMX coprocessors, allow rapid computation of the required FFT functions. All three velocity estimation systems can be implemented in software on current microprocessors, such as the Intel Pentium, or digital signal processors (DSP).

Methods employing contrast agents have been developed to enhance certain imaging methods. Stabilized microbubbles are used for ultrasound contrast imaging because of their unique acoustic properties compared to biological tissues. They present superior backscattering and nonlinear behavior, and fragility upon exposure to ultrasound. A number of ultrasound imaging modalities have been created to exploit these features.

In fundamental B-Mode imaging, the transmitting and receiving frequencies are the same. The echogenicity of blood is significantly increased with the administration of a contrast material. Gas microbubbles scatter sound much more intensely than an equivalent size liquid or solid particle owing to the acoustic impedance mismatch (particularly the difference in compressibility) between the gas and the surrounding tissue or blood. This effect will be observed in Doppler and M-Mode imaging techniques as well. One disadvantage of using fundamental B-Mode for contrast imaging is that the level of the echoes created by the bubbles is similar to the level of the echoes resulting from the biological tissues.

A technique using the second harmonic relies on the fact that bubbles generate harmonics of the transmitted frequency at a level much higher than the harmonics generated by the tissues. By creating images from the signal received at twice the transmitted frequency, high image contrast is achieved between regions with and without bubbles. A problem with this imaging modality is that a short pulse (typically used in B-mode imaging) has a broad bandwidth and the transmitting and receiving frequencies overlap, contaminating the harmonic image with the fundamental frequency. To alleviate this problem, the pulse length is increased to achieve a narrow bandwidth, however, at the expense of decreasing the axial resolution of the image.

The pulse inversion method (also called wideband harmonic imaging or dual pulse imaging), solves the problem of overlapping frequencies observed with the second harmonic technique. Each scan line is formed by summing the signals received from two ultrasound pulses, where the second pulse is inverted and slightly delayed relative to the first. This procedure cancels the response of all linear scatters (if there is no tissue movement between the two pulses) while enhancing the effects of nonlinear scatterers. Because there is delay between the two pulses, any bubble displacement adds an additional signal, resulting in velocity-dependent enhancement.

Because most ultrasound contrast agents are destroyed by ultrasound irradiation, intermittent or gated imaging techniques have been used. By acquiring an image frame at each cardiac cycle (or after several cardiac cycles), ultrasound exposure is reduced, increasing the longevity of the contrast agents in the region of interest on the image. Another benefit of intermittent imaging is the filling of vascular space during the off-cycle. The degree of filling produces enhancement that is directly related to blood volume of blood flow, since the higher flow rate, the greater the number of bubbles that enters the region of interest, and thus the greater the fractional blood volume.

The stimulated acoustic emission method (also known as transient response imaging) typically involves color Doppler with the transmitting power set high to ensure bubble disruption with the first pulse. When the bubbles collapse, a broadband acoustic signal is generated. Since ultrasound Doppler systems compare the backscattered signal with respect to a "clean" reference signal, this loss of frequency correlation caused by the bubble collapse is interpreted by the machine as a random Doppler shift, resulting in a mosaic of colors at the location of the microbubbles.

A preferred embodiment of the invention employs a spatial filter in providing a power doppler image, for example. This spatial or high pass filter can also be used effectively with a contrast agent to further differentiate between blood flow and the surrounding vessel or artery. First the power is computed and a two pulse canceller is employed. The ratio of the power of the signal before and after the filter provides a data set yielding clear images of moving fluid within the body.

While this invention has been particularly shown and described with references to preferred embodiments thereof, it will be understood by those skilled in the art that various changes in form and details may be made therein without departing from the spirit and scope of the invention as defined by the appended claims.

What is claimed is:

1. An ultrasound imaging system comprising:
    a probe housing having a transducer array;
    a first circuit board assembly having a beamforming circuit;
    a second circuit board assembly having a memory, a system controller integrated circuit and a digital communication control circuit;
    a connector that electrically connects the first circuit board to the second circuit board, wherein the first circuit board assembly and the second circuit board assembly are mounted in an interface housing that is connected to the probe housing with a first cable; and
    a personal computer connected to the digital communication control circuit with a standard communication interface such that the personal computer receives a beamformed representation of a region of interest, the personal computer storing instructions to process and display the beamformed representation.

2. The system of claim 1 wherein the personal computer comprises a body mounted system.

3. The system of claim 1 wherein the interface housing comprises a body mounted system.

4. The system of claim 1 wherein the interface housing comprises a body mounted system.

5. The system of claim 1 wherein the memory further comprises a video random access memory (VRAM).

6. The system of claim 1 wherein the standard communication interface comprises an IEEE 1394 interface.

7. The system of claim 1 wherein the standard communication interface comprises a universal serial bus (USB) interface.

8. The system of claim 1 further comprising a third circuit board assembly having a second memory circuit and a second beamforming circuit, the beamforming circuit being connected to the system controller on the second circuit board assembly.

9. The system of claim 1 wherein the memory comprises a synchronous dynamic random access memory (SDRAM).

10. The system of claim 8 further comprising a third memory on the first circuit board assembly.

11. The system of claim 1 wherein the system controller comprises a readout controller, a communications controller, an arbiter and a refresh controller.

12. The system of claim 1 further comprising a transmit/receive circuit mounted in the probe housing.

13. The system of claim 1 further comprising an amplifier/time gain control circuit in the probe housing.

14. The system of claim 1 further comprising a control panel such that a user can control study parameters with the control panel.

15. The system of claim 14 further comprising a control panel mounted on a keyboard of the personal computer.

16. The system of claim 14 wherein the control panel comprises a remote control having a wireless connection to the personal computer.

17. The system of claim 14 wherein the control panel comprises an interface housing.

18. The system of claim 1 further comprising a variable clock generator that can adjust the operating frequency of the transducer array.

19. The system of claim 1 further comprising a DC-DC converter.

20. The system of claim 1 further comprising an interface such that isochronous data is transmitted along the interface.

21. The system of claim 1, further comprising the personal computer storing a set of instructions to perform scan conversion on the beamformed representation.

22. The system of claim 1 further comprising the personal computer storing a set of instructions to process and display ultrasound images.

23. A method of ultrasound imaging comprising:
providing a probe housing having a transducer array that is connected to a first circuit board assembly having a beamforming circuit and a second circuit board assembly having a memory, a system controller integrated circuit and a digital communication control circuit;
connecting the digital communication control circuit to a personal computer with a standard communication interface; and
forming an image of a region of interest in a display in communication with the personal computer in response to the personal computer receiving and processing a beamformed electronic representation of the region of interest.

24. The method of claim 23 further comprising providing an interface housing in which the first circuitry board assembly and the second circuit board assembly are mounted.

25. The method of claim 23 further comprising providing a body mounted personal computer.

26. The method of claim 24 further comprising providing a body mounted interface housing.

27. The method of claim 23 further comprising transmitting data with a IEEE 1394 interface.

28. The method of claim 23 further comprising transmitting data with a universal serial bus (USB) interface.

29. A computer readable medium having stored therein instructions for causing a processing system to execute instructions to process and display the beamformed electronic representation of the region of interest and to execute the method of claim 23.

30. An ultrasound imaging system comprising:
a probe housing having a transducer array;
a circuit board assembly having a beamforming circuit, a memory, a system controller integrated circuit and a communication circuit, the circuit board assembly being mounted in an interface housing that is connected to the probe housing with a first cable; and
a body mounted personal computer connected to the communication control circuit with a standard communication interface such that the personal computer receives a beamformed representation of a region of interest, the personal computer storing instructions to process and display the beamformed representation.

31. The system of claim 30 wherein the interface housing comprises a body mounted system.

32. The system of claim 30 wherein the memory further comprises a video random access memory (VRAM).

33. The system of claim 30 wherein the standard communication interface comprises an IEEE 1394 interface.

34. The system of claim 30 wherein the standard communication interface comprises a universal serial bus (USB) interface.

35. The system of claim 30 further comprising a third circuit board assembly having a second memory circuit and a second beamforming circuit, the beamforming circuit being connected to the system controller on the second circuit board assembly.

36. The system of claim 30 wherein the memory comprises a synchronous dynamic random access memory (SDRAM).

37. The system of claim 30 wherein the system controller comprises a readout controller, a communications controller, an arbiter and a refresh controller.

38. The system of claim 30 further comprising an interface such that isochronous data is transmitted along the interface.

39. The system of claim 30 further comprising the personal computer storing a set of instructions to perform scan conversion on the beamformed representation.

40. The system of claim 30 further comprising the personal computer storing a set of instructions to process and display ultrasound images.

* * * * *